US012714724B2

(12) United States Patent
Springate et al.

(10) Patent No.: US 12,714,724 B2
(45) **Date of Patent: *Aug. 25, 2026**

(54) LOW ENDOTOXIN FUCAN COMPOSITIONS, SYSTEMS AND METHODS

(71) Applicant: ARC Medical Inc., Richmond (CA)

(72) Inventors: Christopher Michael Kevin Springate, Richmond (CA); Ian Millet, Richmond (CA); Sailesh Haresh Daswani, Richmond (CA); Hesong Sun, Richmond (CA); Aileen Shao Ting Yang, Richmond (CA); Hoi Ting Wong, Richmond (CA)

(73) Assignee: ARC Medical Inc., Richmond (CA)

( * ) Notice: Subject to any disclaimer, the term of this patent is extended or adjusted under 35 U.S.C. 154(b) by 199 days.

This patent is subject to a terminal disclaimer.

(21) Appl. No.: 18/403,125

(22) Filed: Jan. 3, 2024

(65) Prior Publication Data

US 2024/0398851 A1 Dec. 5, 2024

Related U.S. Application Data

(62) Division of application No. 17/260,266, filed as application No. PCT/CA2019/051026 on Jul. 24, 2019, now Pat. No. 11,938,145.

(60) Provisional application No. 62/861,228, filed on Jun. 13, 2019, provisional application No. 62/861,235, filed on Jun. 13, 2019, provisional application No. 62/861,223, filed on Jun. 13, 2019, provisional application No. 62/793,514, filed on Jan. 17, 2019, provisional application No. 62/793,654, filed on Jan. 17, 2019, provisional application No. 62/755,311, filed on Nov. 2, 2018, provisional application No. 62/755,328, filed on Nov. 2, 2018, provisional application No. 62/755,318, filed on Nov. 2, 2018, provisional application No. 62/722,137, filed on Aug. 23, 2018, provisional application No. 62/722,135, filed on Aug. 23, 2018, provisional application No. 62/713,413, filed on Aug. 1, 2018, provisional application No. 62/713,392, filed on Aug. 1, 2018, provisional application No. 62/713,399, filed on Aug. 1, 2018, provisional application No. 62/711,364, filed on Jul. 27, 2018, provisional application No. 62/711,372, filed on Jul. 27, 2018, provisional application No. 62/711,335, filed on Jul. 27, 2018.

(51) Int. Cl.

| | |
|---|---|
| ***A61K 31/737*** | (2006.01) |
| ***A61K 47/02*** | (2006.01) |
| ***A61P 41/00*** | (2006.01) |
| ***C08B 37/00*** | (2006.01) |

(52) U.S. Cl.

CPC ............ *A61K 31/737* (2013.01); *A61K 47/02* (2013.01); *A61P 41/00* (2018.01); *C08B 37/0003* (2013.01); *C08B 37/0063* (2013.01)

(58) Field of Classification Search

CPC .......................... A61K 31/737; C08B 37/0063

See application file for complete search history.

(56) References Cited

PUBLICATIONS

Fitton, Mar. Drugs 2015, 13, 5950-5946. (Year: 2015).*

Kopplin, ACS Appl. Bio Mater. 2018, 1, 1880-1892. (Year: 2018).*

Du,A.etal "Purificaiton of theexopolysaccahride produced by Alteromanasinfernus . . ."Appl. Microbiol. Biotechnol.,vol. 101,pp. 6597-6606. (Year: 2017).*

Wang, F.etal "Influence of fucoidan extracts from different fucus species . . ."Mar. Drugs,vol. 19,No. 194, pp. 1-22. (Year: 2021).*

Kopplin, ACS Appl. Bio Mater. 2018, 1, 1880-1892, supporting information. (Year: 2018).*

* cited by examiner

*Primary Examiner* — Layla D Berry

(74) *Attorney, Agent, or Firm* — King IP Law; Joshua King

(57) ABSTRACT

Fucan-low endotoxin compositions comprising a therapeutically effective, medically acceptable fucan in a composition comprising less than about 0.2, 0.18, 0.1, 0.01, 0.001, or 0.0005 endotoxin units (EU) per milligram of the fucan.

27 Claims, 4 Drawing Sheets

LOW ENDOTOXIN FUCAN COMPOSITIONS, SYSTEMS AND METHODS

CLAIM FOR PRIORITY

The present application claims priority to U.S. patent application Ser. No. 17/266,260, filed Jan. 14, 2021, which is a 371 of International Patent Application No. PCT/CA2019/051026 filed Jul. 24, 2019, which claims the benefit of U.S. provisional patent application No. 62/711,364, filed Jul. 27, 2018; U.S. provisional patent application No. 62/711,322, filed Jul. 27, 2018; U.S. provisional patent application No. 62/711,335, filed Jul. 27, 2018; U.S. Provisional Patent Application Ser. No. 62/713,399, filed Aug. 1, 2018; U.S. provisional patent application No. 62/722,135, filed Aug. 23, 2018; U.S. provisional patent application No. 62/755,311, filed Nov. 2, 2018; U.S. provisional patent application No. 62/793,514, filed on Jan. 17, 2019; U.S. provisional patent application No. 62/861,223, filed Jun. 13, 2019; U.S. Provisional Patent Application Ser. No. 62/713,392, filed Aug. 1, 2018; U.S. provisional patent application No. 62/713,413, filed Aug. 1, 2018; U.S. provisional patent application No. 62/722,137, filed Aug. 23, 2018; U.S. provisional patent application No. 62/755,318, filed on Nov. 2, 2018; U.S. provisional patent application No. 62/861,228, filed Jun. 13, 2019; U.S. Provisional Patent Application Ser. No. 62/755,328, filed Nov. 2, 2018; U.S. provisional patent application No. 62/793,654, filed Jan. 17, 2019; and, U.S. provisional patent application No. 62/861,235, filed Jun. 13, 2019, all of which applications are incorporated herein by reference in their entirety.

BACKGROUND

Fucans (including fucoidan) are sulfated polysaccharides. In general terms, this means that they are molecules made up of a number of sugar groups, and also have sulfur atoms attached to the sugar groups. The main sugar group is called "fucose", which is sugar that has 6 carbon atoms and has the chemical formula $C_6H_{12}O_5$. "Fucoidan" (or fucoidin) indicates fucans derived from brown algae (seaweed). Fucans can exist alone, or in a mixture of other sugars, for example in a mixture of sugars such as xylose, galactose, glucose, glucuronic acid and/or mannose. These other sugars may be extracted from the seaweed or other source with the fucan. Although fucans are currently derived from natural sources such as the brown algae (seaweeds), sea cucumbers, etc., mentioned herein, "fucan" includes polymer molecules having the chemical and structural motifs of the fucans as discussed herein regardless of the ultimate source(s) of the fucans.

Fucoidan can be obtained from a variety of species of brown algae including but not limited to: *Adenocystis utricularis, Ascophyllum nodosum, Chorda filum, Cystoseirabies marina, Durvillaea antarctica, Ecklonia kurome, Ecklonia maxima, Eisenia bicyclis, Fucus evanescens, Fucus vesiculosis, Hizikia fusiforme, Himanthalia Elongata, Kjellmaniella crassifolia, Laminaria brasiliensis, Laminaria cichorioides, Laminaria hyperborea, Laminaria japonica, Laminaria saccharina, Lessonia trabeculata, Macrocystis pyrifera, Pelvetia fastigiata, Pelvetia Canaliculata, Saccharina japonica, Saccharina latissima, Sargassum stenophylum, Sargassum thunbergii, Sargassum confusum, Sargassum fusiforme* and *Undaria pinnatifida*. These exemplary species are all from the taxonomic class Phaeophyceae and the majority of these species fall into the families of Fucales and Laminariaceae.

Fucans including fucoidan have been shown to be efficacious in serving to inhibit, prevent, remove, reduce, or otherwise treat the formation of fibrous adhesions. They have also found use in the treatment of other related diseases and conditions.

Lipopolysaccharides, also known as endotoxins, are toxic molecules kept within a bacterial cell and released upon destruction of the bacterial cell wall or secreted from the bacterial cell wall as part of the physiological activity of the bacteria. There are many well established methods in the art for the separation of endotoxin from a molecule of interest. These methods, while efficient for most applications, do not work adequately in the presence of fucans. Part of the reason for this is that many of these methods rely on the isolation of the endotoxins based on negatively charged phosphate groups. In the presence of fucans these methods suffer interference effects from the sulfate groups present on fucan molecules. Other known methods involving chemical treatments result in degradation of the fucan which can be an undesirable effect. The current disclosure addresses cost effective, scalable, and/or non-destructive methods for degradation, elimination and/or removal of endotoxins and other impurities from fucan compositions such as feedstock fucans, and/or other advantages.

SUMMARY

Compositions and methods, etc., herein comprise fucan-low endotoxin compositions having a low level of endotoxins that are suitable for medical and surgical applications, for example, the inhibition, prevention, removal, reduction, or other treatment of fibrous adhesions. These fucan-low endotoxin compositions reduce dangerous complications during the medical and surgical use of fucans due to endotoxins such as inflammation, fever and endotoxemia. Such reductions of endotoxins can be from about a 95% reduction to about a 99%, 99.9%, 99.99%, 99.999%, 99.9999% to 99.99999% reduction. In certain embodiments, the fucan compositions presented herein have endotoxin levels low enough to render the compositions suitable for medical and surgical applications.

The fucan-low endotoxin compositions presented herein provide compositions of a desired fucan composition obtained from a starting or initial fucan composition (i.e., fucan compositions from which the fucan-low endotoxin compositions can be derived; such starting fucan compositions may or may not be crude or have been previously processed or purified, such as a feedstock fucan composition) as well as methods of obtaining such desired fucan-low endotoxin compositions and methods of use of such compositions.

In some aspects, the compositions, systems, methods, etc., herein comprise fucan-low endotoxin compositions can comprise less than about 0.2, 0.18, 0.16, 0.1, 0.09, 0.06, 0.04, 0.03, 0.02, 0.01, 0.007, 0.003, 0.002, 0.001, 0.0006, or 0.0005 endotoxin units per milligram of the fucan.

In some embodiments, The fucans can have a molecular weight distribution wherein at least 60% w/w of the distribution can be greater than 100 kDa when measured using an aqueous gel permeation chromatography set up consisting essentially of:

one 300 mm analytical gel permeation chromatography column with a 7.8 mm inner diameter packed with hydroxylated polymethacrylate-based gel, having an effective molecular weight range of between about 50 kDa and about 5,000 kDa, one 300 mm analytical gel permeation chromatography column with a 7.8 mm inner diameter packed with hydroxylated polymethacrylate-based gel, having an effective molecular weight range of between about 1 kDa and about 6,000 kDa and one 40 mm guard column with a 6 mm inner diameter packed with hydroxylated polymethacrylate-based gel, the two analytical gel permeation chromatography columns and the one guard column contained in a column compartment at about 30° C.;

a refractive index detector at about 30° C.;

0.1 M sodium nitrate mobile phase run at 0.6 mL/min; and quantification against a peak molecular weight standard curve consisting essentially of a first dextran standard with a peak molecular weight of about 2,200 kDa, a second dextran standard with a peak molecular weight of between about 720 kDa and about 760 kDa, a third dextran standard with a peak molecular weight between about 470 kDa and about 510 kDa, a fourth dextran standard with a peak molecular weight between about 370 kDa and about 410 kDa, a fifth dextran standard with a peak molecular weight between about 180 kDa and about 220 kDa, and a sixth dextran standard with a peak molecular weight between about 40 kDa and 55 kDa.

The fucans can have a molecular weight distribution wherein at least: 75% w/w of the distribution can be greater than 100 kDa; 98% w/w of the distribution can be greater than 100 kDa; 81% w/w of the distribution can be greater than 200 kDa; 92% w/w of the distribution can be greater than 200 kDa; 97% w/w of the distribution can be greater than 200 kDa; 44% w/w of the distribution can be greater than 500 kDa; 61% w/w of the distribution can be greater than 500 kDa; 70% w/w of the distribution can be greater than 500 kDa; 80% w/w of the distribution can be greater than 500 kDa; 5% w/w of the distribution can be greater than 1600 kDa; 10% w/w of the distribution can be greater than 1600 kDa; 24% w/w of the distribution can be greater than 1600 kDa; 31% w/w of the distribution can be greater than 1600 kDa. Further, The fucans can have a weight average molecular weight greater than 100 kDa; greater than 200 kDa or greater than 500 kDa.

The fucans can have a sulfation level of between about 20% w/w and 60% w/w, between about 30% w/w and 55% w/w, between about 32% w/w and 52% w/w. The fucans can have a total carbohydrate content of between 27% w/w and 80% w/w and a total fucose content as a percentage of the total carbohydrate content of at least about 30% w/w, 50% w/w, 70% w/w, 80% w/w, 90% w/w, or 95% w/w. The fucans can have a total galactose content as a percentage of the total carbohydrate content below about 60% w/w, between about 2% w/w and 20% w/w, or below about 10% w/w.

The fucan-low endotoxin compositions when dissolved in water at a concentration of 50 mg/mL can have a viscosity of between about 4 cP and 50 cP, between about 10 cP and 40 cP, or between about 15 cP and 30 cP. The fucan-low endotoxin compositions can be a white solid, and when dissolved in water at a concentration from 1 mg/mL through 100 mg/mL forms a solution that can be one of clear-colorless. The fucans can comprise less than 5% or 2% w/w acetyl content. Further, the fucans can comprise an acetyl content of substantially 0% w/w when measured by 2D $^{1}H$-$^{13}C$ heteronuclear multiple quantum coherence at 70° C. with solvent signal suppression on a 600 MHz spectrometer equipped with 5-mm cold probe, in the range from 10-30 ppm in the carbon dimension, in 8 increments of 256-512 scans each.

Also included herein are methods of making and using the fucans and fucan-low endotoxin compositions herein. The using can comprise treating fibrous adhesions.

In certain aspects, the compositions, systems, methods, etc., herein comprise medically acceptable fucan-low endotoxin compositions can comprise a therapeutically effective amount of the fucan-low endotoxin compositions herein in a medically acceptable buffer or diluent. Also provided are fucan-low endotoxin dosages that can comprise the medically acceptable fucan-low endotoxin compositions herein wherein the medically acceptable fucan-low endotoxin dose has an endotoxin level equal to or below 250 EU, 50 EU, 20 EU, 10 EU, 2 EU, 1 EU, 0.1 EU, or 0.01 EU. Such medically acceptable fucan-low endotoxin compositions and dosages can have the molecular weight distributions and other parameters discussed herein such as in the paragraphs above.

In further aspects, the compositions, systems, methods, etc., herein comprise methods of treating a condition or disease in an animal that can comprise selecting the medically acceptable fucan-low endotoxin compositions to treat the condition or disease and administering a therapeutically effective amount can comprise at or between about 0.5 mg/kg and 50 mg/kg of the fucans to the animal. The amounts can also be at or between about 0.04 mg/kg and 25 mg/kg, about 0.2 mg/kg and 10 mg/kg, about 1 mg/kg and 5 mg/kg, 0.5 mg/kg and 3 mg/kg, or 5 mg/kg and 10 mg/kg.

The condition or disease can be a fibrous adhesion at a target site in the animal, and the administering can comprise administering the therapeutically effective amount to the target site. The medical compositions can comprise between about 0.02 mg/mL and 100 mg/mL of the fucan from fucan-low endotoxin compositions herein, and the medical composition can be configured and composed to treat a disease or condition in an animal. The amounts can also be at or between about 0.5 mg/mL and 5 mg/mL, or about 2.5 mg/mL. The medical composition can be a medical device, which can be a liquid medical device. The medical composition can be a pharmaceutical composition, including a liquid pharmaceutical composition.

The methods herein include use of a dosages range that can comprise between about 0.01 mL/kg and 15 mL/kg of the medical compositions to treat a disease or condition in an animal. The amounts can also be at or between about, 0.03 mL/kg and 4 mL/kg, 0.06 mL/kg and 2 mL/kg, or 2 mL/kg and 4 ml/kg.

The methods for treating fibrous adhesions in a patient can comprise administering the medical compositions to a target site in the patient. The target site can be a surgical site and the administering can be performed at least one of a) after opening a surgical wound at the surgical site, b) during surgery, and c) after closing the surgical wound, including after surgery but before closing the surgical wound. The administering can take less than 3 minutes, 2 minutes, or 1 minute. The target site can be at least one of a lesion, abrasion and injury site. The target site can be at least one of a pelvic cavity, an abdominal cavity, a dorsal cavity, a cranial cavity, a spinal cavity, a ventral cavity, a thoracic cavity, a pleural cavity, a pericardial cavity, skin, a joint, a muscle, a tendon and a ligament.

In other aspects, the compositions, systems, methods, etc., herein comprise methods for removing impurities from a starting fucan composition to obtain fucan-low endotoxin compositions. Such methods can comprise:

providing a starting fucan composition comprising impurities;

adding a flocculation aid to the starting fucan composition to produce a reaction mixture;

flocculating the impurities by heating the reaction mixture to produce flocculated impurities;

and removing the flocculated impurities.

The providing the starting fucan composition can comprise providing the starting fucan composition as a solution, and the method further can comprise collecting the fucan-low endotoxin compositions in a reduced-impurities solution. The methods can further comprise flocculating the impurities by heating the reaction mixture in excess of atmospheric pressure. The flocculation aid can comprise a salt, which can be a chloride, bromide, iodide, fluoride, sulfate, sulfite, carbonate, bicarbonate, phosphate, nitrate, nitrite, acetate, citrate, silicate and/or cyanide of an alkali metal, alkaline earth metal, aluminum and/or ammonium. The flocculation aid can comprise a base, which can be a hydroxide and/or oxide of an alkali metal, alkaline earth metal, aluminum and/or ammonium.

Further methods can comprise:

providing a starting fucan composition comprising impurities and a disrupting agent capable of disrupting cells and endotoxin aggregation in a solution; and subjecting the solution to tangential flow filtration across a tangential flow filtration filter to produce a retentate fucan composition that can comprise the fucan-low endotoxin compositions and residual disrupting agent.

Removing the residual disrupting agent can be achieved by tangential flow filtration across a tangential flow filtration filter to produce a second retentate fucan composition that can comprise the fucan-low endotoxin compositions. The methods further can comprise:

removing the residual disrupting agent by treating the retentate fucan composition with a precipitating agent capable of precipitating the disrupting agent to produce a precipitate of the disrupting agent and a supernatant fucan composition; and separating the precipitate of the disrupting agent from the supernatant fucan composition.

The methods further can comprise collecting the fucan-low endotoxin compositions in a reduced-impurities solution. The disrupting agent can comprise at least one detergent, which can be an anionic detergent, a cationic detergent or a non-ionic detergent. The detergent can comprise at least one of sodium dodecyl sulfate (SDS), benzalkonium chloride, Triton® X 100, Triton® X 114 and sodium deoxycholate.

The precipitating agent can comprise at least one of potassium chloride, potassium hydroxide, calcium chloride, barium chloride and calcium carbonate. Further methods can comprise:

providing a starting fucan composition as a solid and an extraction media incapable of dissolving fucans, configured for dissolving impurities;

mixing the starting fucan composition with the extraction media to produce a mixture of the fucan-low endotoxin compositions and the extraction media; and separating the fucan-low endotoxin compositions from the extraction media.

The methods further can comprise collecting the fucan-low endotoxin compositions as a solid. The extraction media can comprise at least one organic solvent with a relative polarity less than 0.765. The organic solvent can comprise at least one of ethanol, isopropanol, methanol, benzene, diethyl ether, decamethylcyclo-pentasiloxane, ethyl acetate, butanol, hexane, heptane, heptanol, octanol and decanol. The extraction media further can comprise at least one of a base, a detergent and an oxidizing agent. The providing the starting fucan composition in a solid form that can comprise precipitating the starting fucan composition from a solution. The fucan-low endotoxin compositions contain less endotoxin than the starting fucan composition.

Still further methods can comprise:

providing a starting fucan composition comprising impurities, including suspended impurities in a solution;

precipitating the impurities from the solution using an ionic-multivalent impurity precipitant, thereby producing a mixture of suspended impurities, precipitated impurities and a supernatant solution; and separating the suspended impurities and precipitated impurities from the supernatant solution.

The methods further can comprise collecting the supernatant solution that can comprise the fucan-low endotoxin compositions. The ionic-multivalent impurity precipitant can comprise a salt of a divalent or trivalent cation. The salt can be a chloride, bromide, iodide, fluoride, sulfate, sulfite, carbonate, bicarbonate, phosphate, nitrate, nitrite, acetate, citrate, silicate and/or cyanide. The cation can be an alkaline earth metal, zinc, aluminum, copper and/or iron. The impurity precipitant can comprise a base of a divalent or trivalent cation. The base can be a hydroxide and/or oxide of an alkaline earth metal, zinc, aluminum, copper and/or iron. The separating the suspended impurities and precipitated impurities from the supernatant solution can comprise flocculating the suspended impurities and precipitated impurities by adding a flocculant to the mixture of suspended impurities, precipitated impurities and supernatant solution. The flocculant can comprise at least one of potassium aluminum sulfate; sodium aluminum sulfate; ammonium aluminum sulfate; calcium chloride; sodium phosphate; aluminum hydroxide; aluminum chloride; ferric chloride; ferric sulfate; ferrous sulfate; sodium silicate; calcium silicate; calcium phosphate; zinc chloride; calcium carbonate; calcium bicarbonate; potassium sulfate; magnesium phosphate; acrylamides; acrylic acid; aluminum chlorohydate; polyaluminium chloride; tannins; formaldehyde; melamine; N,N-dimethylaminocthyl acrylate methyl chloride; N,N-dimethylaminocthyl methacrylate methyl chloride quaternary; and polydiallyldimethyl-ammonium chloride. The methods further can comprise maintaining a pH of between about 7 and 14; maintaining the pH can comprise the addition of base.

Other methods can comprise:

providing a starting fucan composition comprising impurities;

adjusting the starting fucan composition pH to between about 8 and 14;

adding to the starting fucan composition a cellular disrupting agent configured for lysing cellular components to produce a reaction mixture that can comprise the cellular disrupting agent, biomolecular lysates and the starting fucan composition; and removing the cellular disrupting agent and biomolecular lysates from the reaction mixture.

Providing the starting fucan composition can comprise providing the starting fucan composition as a solution. The methods further can comprise collecting the fucan-low endotoxin compositions in a reduced-impurities solution. The cellular disrupting agent can comprise a detergent. The detergent can be an anionic detergent, a cationic detergent or a non-ionic detergent. The detergent can comprise at least one of sodium dodecyl sulfate (SDS), benzalkonium chloride, Triton X 100®, Triton X 114®, Brij® detergents, Tween® detergents, sodium deoxycholate, and alkylbenzenesulfonates.

Removing the cellular disrupting agent and biomolecular lysates can comprise adding to the reaction mixture a flocculant configured for flocculating the cellular disrupting agent and biomolecular lysates. The removing the cellular disrupting agent can comprise adding to the reaction mixture a precipitant capable of rendering the cellular disrupting agent insoluble in the reaction mixture, producing precipitates. The removing the biomolecular lysates can comprise adding to the reaction mixture a precipitant configured for rendering the biomolecular lysates insoluble in the reaction mixture, producing precipitates. The methods further can comprise adding to the reaction mixture a flocculant configured for flocculating the precipitates. The flocculant can comprise at least one of potassium aluminum sulfate; sodium aluminum sulfate; ammonium aluminum sulfate; calcium chloride; sodium phosphate; aluminum hydroxide; aluminum chloride; ferric chloride; ferric sulfate; ferrous sulfate; sodium silicate; calcium silicate; calcium phosphate; zinc chloride; calcium carbonate; calcium bicarbonate; potassium sulfate; magnesium phosphate; acrylamides; acrylic acid; aluminum chlorohydate; polyaluminium chloride; tannins; formaldehyde; melamine; N,N-dimethylaminoethyl acrylate methyl chloride; N,N-dimethylaminoethyl methacrylate methyl chloride quaternary; and polydiallyldimethyl-ammonium chloride. Removing the anionic detergent can comprise anionic adsorption. Removing the cationic detergent can comprise cationic adsorption; removing the non-ionic detergent can comprise micellar phase separation; removing the detergent can comprise hydrophobic adsorption.

Removing the detergent can comprise:

diluting the reaction mixture until the concentration of the detergent can be below a predetermined concentration; and subjecting the reaction mixture comprising the detergent to diafiltration over a tangential flow filtration filter with a molecular weight cut-off above the largest molecular weight of the detergent.

The methods further can comprise adding a chelating agent to the reaction mixture after providing the starting fucan composition and before removing the cellular disrupting agent. The chelating agent can comprise ethylenediaminetetraacetic acid (EDTA), 2,3-dimercapto-1-propanol, ethylene diamine, porphine and/or citric acid. The methods also can comprise adding an oxidant-quenching agent to the reaction mixture before removing the cellular disrupting agent to quench oxidants in the reaction mixture. The methods further can comprise adding a bacteriostatic agent to the reaction mixture after providing the starting fucan composition and before removing the cellular disrupting agent. The bacteriostatic agent can comprise sodium sulfite, ethylenediaminetetraacetic acid (EDTA), benzalkonium chloride, ethanol, and/or thiourea.

Still other methods can comprise:

providing a starting fucan composition comprising endotoxins, and an anion-exchange macroporous resin;

subjecting the starting fucan composition to anion-exchange with the anion-exchange macroporous resin to produce the fucan-low endotoxin compositions.

The methods further can comprise pre-treating the starting fucan composition with a disrupting agent capable of disrupting aggregation of the endotoxins, and can comprise desalting the starting fucan composition before subjecting the starting fucan composition to anion-exchange with the anion-exchange macroporous resin. The anion-exchange macroporous resin can have a pore size greater than the average hydrodynamic radius of the endotoxins in the starting fucan composition. The providing the starting fucan composition and the anion-exchange macroporous resin can comprise providing the starting fucan composition and the anion-exchange macroporous resin at a mass ratio of the starting fucan composition: anion-exchange macroporous resin of between about 1:100 and about 10:1. The mass ratio can also be between about 1:50 and about 1:1, or about 1:10 and about 1:1. The starting fucan composition can be subjected to anion-exchange for a period of between about 5 minutes and about 100 hours, or between about 1 hour and about 30 hours. The anion-exchange macroporous resin can comprise quaternary amine groups. The anion-exchange macroporous resin can comprise at least one of primary, secondary and tertiary amine groups. The anion-exchange macroporous resin can be composed of at least one of styrene, agarose, dextran, acrylate, methacrylate, methyl methacrylate, butyl methacrylate, divinylbenzene, cellulose, silica, and ceramic. The anion-exchange macroporous resin can have a pore size of between about 5 nm and about 1000 nm, or between about 10 nm and about 100 nm, or between about 15 nm and about 50 nm. The anion-exchange macroporous resin can have an exclusion limit of between about 5 kDa and about 50,000 kDa, or between about 1,000 kDa and about 9,000 kDa, or between about 5 kDa and about 200 kDa.

Still other further methods can comprise:

providing a starting fucan composition comprising impurities in an aqueous starting solution;

mixing the aqueous starting solution with an organic solvent to produce an aqueous-organic phase mixture; and separating the aqueous-organic phase mixture to obtain an aqueous portion and an organic portion.

The collecting the aqueous portion can comprise the fucan-low endotoxin compositions. The organic solvent can comprise at least one organic solvent with a relative polarity less than 0.765. The values for relative polarity can be normalized from measurements of solvent shifts of absorption spectra. See for example Christian Reichardt, Solvents and Solvent Effects in Organic Chemistry, Wiley-VCH Publishers, 3rd ed., 2003. The organic solvent can comprise at least one of ethanol, isopropanol, methanol, benzene, decamethylcyclo-pentasiloxane, ethyl acetate, hexane, heptanol, octanol, decanol, heptane, isobutyl acetate, anisole, isopropyl acetate, 1-butanol, butyl acetate, methylisobutylketone, pentane, 1-pentanol, ethyl ether, and propyl acetate.

The processed fucan-low endotoxin compositions herein contain less endotoxin than the starting fucan composition.

These and other aspects, features and embodiments are set forth within this application, including the following Detailed Description and attached drawings. Unless expressly stated otherwise, all embodiments, aspects, features, etc., can be mixed and matched, combined and permuted in any desired manner.

Figure 1:
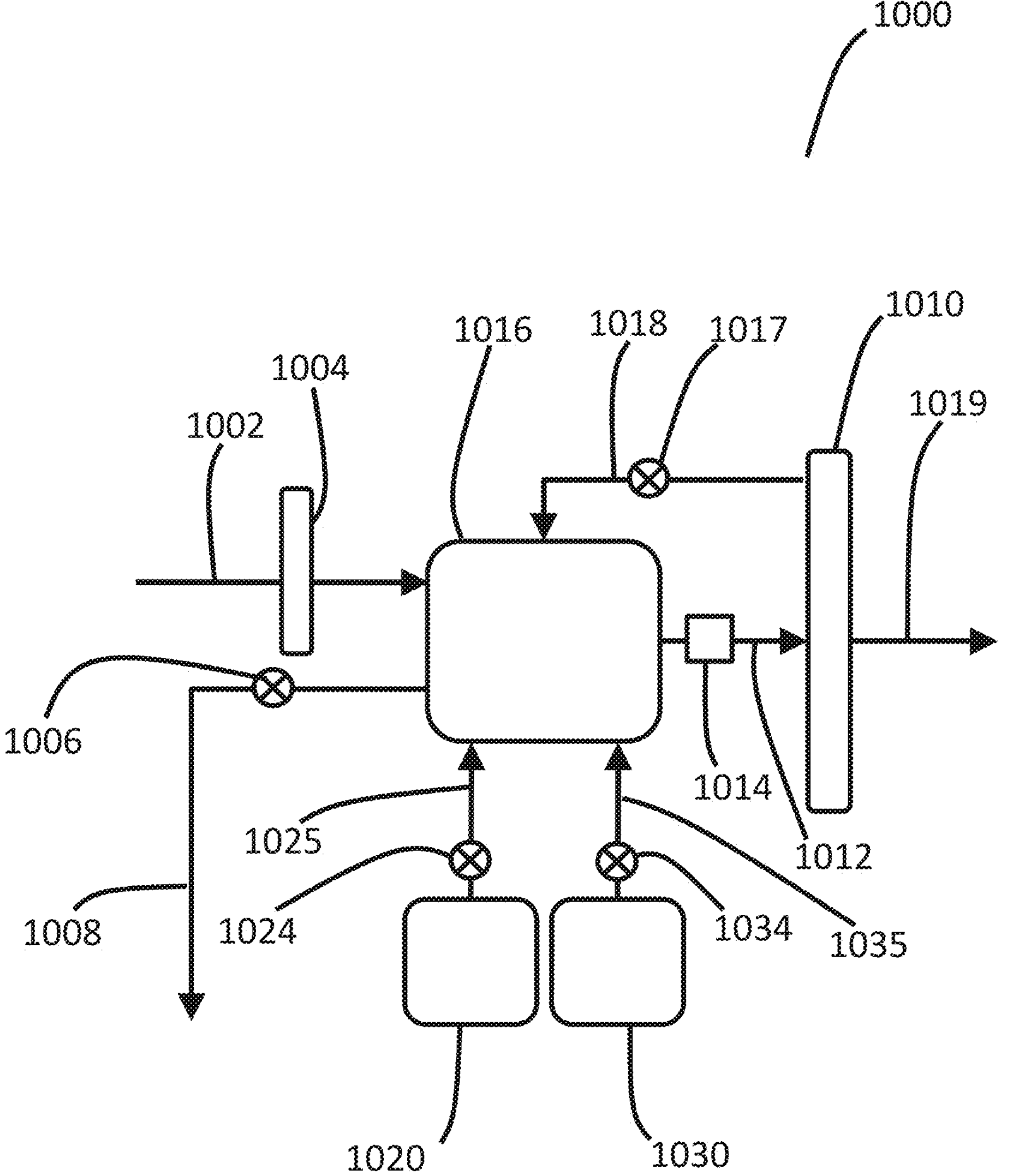
FIG. 1 schematically depicts a tangential flow filtration system for obtaining a reduction in impurities, including endotoxins, of a starting fucan composition.

The drawings present exemplary embodiments of the present disclosure. The drawings are not necessarily to scale and certain features may be exaggerated or otherwise represented in a manner to help illustrate and explain the present systems, methods, etc. Actual embodiments of the systems, methods, etc., herein may include further features or steps not shown in the drawings. The exemplifications set out herein illustrate embodiments of the systems, methods, etc., in one or more forms, and such exemplifications are not to be construed as limiting the scope of the disclosure in any manner. The embodiments herein are not exhaustive and do not limit the disclosure to the precise form disclosed, for example in the following detailed description.

DETAILED DESCRIPTION

The current compositions, systems, methods, etc., presented herein comprise purified fucan compositions, for example fucan-low endotoxin compositions. The present compositions can be effective for medical treatments, post-surgical treatments, disease inhibition, etc. In some embodiments, the fucan is fucoidan. The present fucan-low endotoxin compositions can themselves be, or can be included on or in, medical devices, medical materials, combination products or in pharmaceutically acceptable, therapeutically and/or medically effective compositions.

The following paragraphs turn to a brief general discussion of some of the fucan-low endotoxin compositions herein, including those that can be created using the methodologies discussed herein.

Compositions

The current compositions, systems, etc., presented herein provide, in certain embodiments, fucans and medically acceptable fucan-low endotoxin compositions comprising therapeutically effective amounts of fucans-low endotoxin for the treatment of fibrous adhesions, such as surgical adhesions, arthritis, psoriasis or other diseases as desired.

The fucan-low endotoxin compositions presented herein may be used for a plurality of applications, including the inhibition, prevention, removal, reduction, or other treatment of fibrous adhesions and other targets, diseases and/or conditions. Treatment includes that the compositions reduce or prevent the development of a target disease or other condition, such as reducing or preventing the formation of fibrous adhesions at a target site, which is typically a selected target site identified by a surgeon or other practitioner as comprising or being reasonably susceptible to having fibrous adhesions (or other diseases or conditions), and also includes elimination of existing diseases or other conditions, including for example the elimination of already-existing fibrous adhesions. For such inhibition, prevention, removal, reduction, or other treatment, the fucan composition can be provided in a medically acceptable medical device, medical materials, combination product, or pharmaceutically effective composition that contains additional components such as binders, adjuvants, excipients, etc., as well as, if desired, additional medically active substances such as secondary drugs that are contained within the composition but not attached to the fucan, and/or that can be attached to the fucan.

Thus, in some embodiments, the current disclosure presents fucan-low endotoxin compositions with low levels of endotoxins, which compositions are suitable for medical and surgical applications, for example, the prevention, inhibition or treatment of fibrous adhesions.

In certain aspects and embodiments, the compositions herein comprise a therapeutically effective, medically acceptable fucan comprising less than about 0.2, 0.18, 0.12, 0.1, 0.09, 0.02, 0.01, 0.007, 0.005, 0.002 or 0.001 endotoxin units (EU) per milligram (mg) of the fucan (EU/mg).

The molecular weight distribution of the fucan-low endotoxin compositions may be measured using any desired, appropriate measurement system. Different systems can yield different readings or results from different compositions having essentially the same make-up, or even from the same batch when measured differently. One suitable measurement system is an aqueous gel permeation chromatography set up consisting essentially of one 300 mm analytical gel permeation chromatography column with a 7.8 mm inner diameter packed with hydroxylated polymethacrylate-based gel, having an effective molecular weight range of between about 50 kDa and about 5,000 kDa, one 300 mm analytical gel permeation chromatography column with a 7.8 mm inner diameter packed with hydroxylated polymethacrylate-based gel, having an effective molecular weight range of between about 1 kDa and about 6,000 kDa and one 40 mm guard column with a 6 mm inner diameter packed with hydroxylated polymethacrylate-based gel, the two analytical gel permeation chromatography columns and the one guard column contained in a column compartment at about 30° C., a refractive index detector at about 30° C., 0.1 M sodium nitrate mobile phase run at 0.6 mL/min, and quantification against a peak molecular weight standard curve consisting essentially of a first dextran standard with a peak molecular weight of about 2,200 kDa, a second dextran standard with a peak molecular weight of between about 720 kDa and about 760 kDa, a third dextran standard with a peak molecular weight between about 470 kDa and about 510 kDa, a fourth dextran standard with a peak molecular weight between about 370 kDa and about 410 kDa, a fifth dextran standard with a peak molecular weight between about 180 kDa and about 220 kDa, and a sixth dextran standard with a peak molecular weight between about 40 kDa and 55 kDa. The peak molecular weight standard curve may further comprise a dextran standard with a peak molecular weight between 3 kDa and 5 kDa.

The fucan-low endotoxin compositions herein may further comprise a fucan with a molecular weight distribution in which at least about 25%, 30%, 40%, 50%, 60%, 70%, 75%, 80%, 85%, 90%, 95% and 99% w/w of the fucan has a molecular weight greater than 100 kDa. The fucan-low endotoxin compositions herein may comprise a fucan with a molecular weight distribution in which at least about 50%, 60%, 70%, 80%, 90%, 95% and 99% w/w of the fucan has a molecular weight greater than 200 kDa. The fucan-low endotoxin compositions herein may comprise a fucan with a molecular weight distribution in which at least about 25%, 30%, 40%, 50%, 60%, 70%, 75%, 80%, 85%, 90% w/w of the fucan has a molecular weight greater than 500 kDa. The fucan-low endotoxin compositions herein may comprise a fucan with a molecular weight distribution in which at least about 5%, 10%, 20%, 30%, or 40% w/w of the fucan has a molecular weight greater than 1600 kDa.

The fucan-low endotoxin compositions herein may comprise a fucan with a weight average molecular weight greater than about 100 kDa, for example between about 100 kDa and about 10,000 kDa, between about 200 kDa and about 8,000 kDa, between about 350 kDa and about 7,000 kDa, between about 450 kDa and about 6,000 kDa, between about 580 kDa and about 5,000 kDa, or between 500 kDa and about 2,000 kDa. The fucan-low endotoxin compositions herein may comprise a fucan with a peak molecular weight greater than about 70 kDa, for example between about 70 kDa and about 1200 kDa, between about 100 kDa and about 1200 kDa, between about 200 kDa and about 1200 kDa, between about 400 kDa and about 1200 kDa, or between about 400 kDa and about 900 kDa.

The fucan-low endotoxin compositions herein may comprise a fucan with a number average molecular weight greater than about 50 kDa, between about 50 kDa and about 1,000 kDa, between about 70 kDa and about 1000 kDa, between about 150 kDa and about 1000 kDa, between about 250 kDa and about 1000 kDa, or between about 250 kDa and about 700 kDa.

The fucan in the fucan-low endotoxin compositions herein may have a sulfation level of between about 10% w/w and 70% w/w, between about 20% w/w and 65% w/w, between about 30% w/w and 55% w/w, between about 40% w/w and 60% w/w, or between about 40% w/w and 50% w/w.

The fucan in the fucan-low endotoxin compositions herein may have a molar ratio of total fucose: total sulfate of between about 1:0.5 and 1:4, between about 1:0.8 and 1:3.5, between about 1:1 and 1:2.5, between about 1:1.2 and 1:2.0, or between about 1:1.5 and 1:3. The fucan in the fucan-low endotoxin compositions herein may have a molar ratio of total fucose plus galactose: total sulfate of between about 1:0.5 and 1:4, between about 1:0.8 and 1:3.5, between about 1:1 and 1:2.5, between about 1:1.2 and 1:2.0, or between about 1:1.5 and 1:3.

The fucan in the fucan-low endotoxin compositions herein may have a total carbohydrate content of between about 27% w/w and 80% w/w, 30% w/w and 70% w/w, between about 40% w/w and 90% w/w, between about 48% w/w, or 50% w/w and 96% w/w. The fucan in the fucan-low endotoxin compositions herein may have a fucose content as a percentage of total carbohydrate of between about 30% w/w and 100% w/w, between about 40% w/w and 95% w/w or between about 50% w/w and 90% w/w.

The fucan in the fucan-low endotoxin compositions herein may have a galactose content as a percentage of total carbohydrate of between 0% w/w and 60% w/w, between 0% w/w and 60% w/w, between about 5% w/w and 30% w/w, or between about 0% w/w and 10% w/w or 15% w/w. The fucan in the fucan-low endotoxin compositions herein may have a glucuronic acid content as a percentage of total carbohydrate content between about 0% w/w and 10% w/w, a mannose content as a percentage of total carbohydrate content between about 0% w/w and 7% w/w, a rhamnose content as a percentage of total carbohydrate content between 0% w/w and 4% w/w, and a xylose content as a percentage of total carbohydrate content between 0% w/w and 20% w/w.

In some embodiments, the fucan-low endotoxin compositions herein, when dissolved at a concentration of 50 mg/mL in water, have a viscosity of between about 4 cP and about 50 cP, between about 5 cP and about 40 cP, between about 10 cP and about 30 cP, about 15 cP, about 20 cP and about 25 cP. In certain embodiments, the fucan-low endotoxin compositions herein, when dissolved in water at 1 mg/mL through 100 mg/mL form a solution that is one of clear and colorless, or transparent and light yellow or clear and light brown.

In certain embodiments, the fucans in the fucan-low endotoxin compositions herein can have an acetyl content of less than about 5% w/w, less than about 2% w/w, and about 0% w/w. In some embodiments, the fucans in the fucan-low endotoxin compositions herein comprise substantially 0% w/w acetyl content when measured by 2D $^{1}H$-$^{13}C$ heteronuclear multiple quantum coherence at 70° C. with solvent signal suppression on a 600 MHz spectrometer equipped with 5-mm cold probe, in the range from 10-30 ppm in the carbon dimension, in 8 increments of 256-512 scans each.

Methods

Methods, systems, etc., are provided for purifying, depyrogenating or otherwise reducing the load of impurities in a starting fucan composition such as a feedstock fucan composition. The methods and compositions, etc., comprise eliminating, inactivating or otherwise reducing an undesired amount of, or effect from, endotoxins and other endotoxin-containing components such as biological contaminants, cellular components, etc. to obtain fucan-low endotoxin compositions comprising, for example, less than 0.2, 0.18, 0.12, 0.1, 0.09, 0.03, 0.02, 0.01, 0.007, 0.005, 0.002 or 0.001 endotoxin units (EU) per milligram (mg) of the fucan (EU/mg). Biological contaminants include microorganisms such as bacteria, viruses, yeasts, molds and parasites, some of which produce toxins, and some of which comprise cellular components. Biological contamination, cellular components, endotoxins and other endotoxin-containing components are included in the term impurities as used herein.

In some embodiments, the current disclosure presents fucan-low endotoxin compositions that are suitable for medical and surgical applications, for example, the prevention of fibrous adhesions.

In some of the methods herein, the current disclosure discusses the use of tangential flow filtration (TFF), which TFF can remove or assist in removal of endotoxins. The format of the tangential flow filtration apparatus used can be, for example, one of a plate and frame system; a spiral wound cartridge system; a hollow fiber system; a flow cell system; and a centrifugal filter system.

The following paragraphs turn to a brief discussion of some of the methodologies that can be used to create the fucan-low endotoxin compositions herein from starting fucan compositions via various methods that can be performed using any suitable reaction mixture such as solutions, suspensions, solids, gels or other modalities depending on the chosen method(s).

Physically Induced Flocculation

A starting fucan composition, such as a feedstock fucan composition, comprising high levels of endotoxins undergoes a flocculation of impurities, which can be a physically-induced flocculation. The methods can comprise: providing a starting fucan composition; adding a flocculation aid to the starting fucan composition to produce a reaction mixture; flocculating the impurities in the starting fucan composition by heating the reaction mixture; separating the flocculated impurities from the reaction mixture; and collecting the desired fucan-low endotoxin composition after the separating.

Flocculating the impurities by heating the reaction mixture may comprise heating the reaction mixture while subjecting the reaction mixture to a pressure in excess of atmospheric pressure. Suitable flocculation aids include without limitation, salts and/or bases, for example chlorides, bromides, iodides, fluorides, sulfates, sulfites, carbonates, bicarbonates, phosphates, nitrates, nitrites, acetates, citrates, silicates, oxides, hydroxides and/or cyanides of an alkali metal, alkaline earth metal, aluminum and/or ammonium, for example, sodium chloride, sodium sulfate, potassium chloride, calcium sulfate, sodium phosphate, sodium nitrate, lithium chloride, lithium nitrate, ammonium chloride, sodium carbonate, sodium hydroxide. Separating the flocculated impurities from the reaction mixture may comprise one or more of centrifuging, filtering, sedimentation or hydrodynamic flow separation of the reaction mixture.

The methods, etc., herein may further comprise desalting the starting fucan composition before adding a flocculation aid. The desalting may comprise diafiltrating the starting fucan composition as a solution in water across a molecular weight cutoff (MWCO) tangential flow filtration (TFF) filter. The diafiltrating may comprise diafiltrating the starting fucan composition with distilled water. The molecular weight cutoff TFF filter can have a molecular weight cutoff smaller than a desired molecular weight separation point or target in or for the fucan composition, for example a 50 kDa, 70 kDa, 100 kDa, 200 kDa, 300 kDa, 500 kDa or 1000 kDa molecular weight cut-off.

The methods can be performed in basic and neutral environments. The adding of a flocculation aid to the starting fucan composition may therefore comprise rendering the starting fucan composition basic to prevent or inhibit the fucan in the starting fucan composition from degrading, because fucans are prone to degradation in acidic environments. In other embodiments, the method can be carried out by maintaining the reaction mixture at or near a pH of 7 or more.

In some embodiments, the starting fucan composition may be provided as a solution. Example fucans suitable for treatment by the above method include without limitation fucoidan, and the concentration of the fucan in solution may be between 0.01% w/v and 50% w/v. Impurities that may be removed by the above method include without limitation particulates, lipids, fatty acids, phlorotannins, laminarins, alginates, proteins, Maillard reaction products, fucoxanthin, chlorophyll, free ions, bacteria, viruses, yeasts, molds, parasites, DNA and endotoxins.

Gel Permeation Chromatography

Gel permeation chromatography ("GPC") was employed to evaluate the molecular weight distributions obtained for the experimental examples. There are a large number of different parameters, columns and standards available for use in gel permeation chromatography, resulting in a variety of instrumentation set-ups available for the analysis of molecular weight. For molecular weight determinations herein, the GPC were conducted using the following parameters: The mobile phase was 0.1 M sodium nitrate run at 0.6 mL/min. The column compartment and detector were at 30° C. A Waters 2414 refractive index detector was used for detection.

Suitable GPC columns include GPC columns compatible with aqueous solvents, for example columns packed with at least one of sulfonated styrene-divinylbenzene, NH-functionalized acrylate copolymer network, modified silica and hydroxylated polymethacrylate-based gel. For the analyses herein, three columns were used in series, comprising one 40 mm long guard column with an inner diameter (ID) of 6 mm packed with 6 μm particle size hydroxylated polymethacrylate-based gel, followed by a first 300 mm analytical GPC column with a 7.8 mm ID packed with 12 μm particle size hydroxylated polymethacrylate-based gel that has an exclusion limit of about 7,000 kDa and an effective molecular weight range of between about 50 kDa and about 5,000 kDa, followed by a second 300 mm analytical GPC column with a 7.8 mm ID packed with 10 μm particle size hydroxylated polymethacrylate-based gel that has an exclusion limit of about 7,000 kDa and an effective molecular weight range of between about 1 kDa and about 6,000 kDa. The total effective molecular weight range of the column set up was between about 1 kDa and about 6,000 kDa. An example of this column set up can be Ultrahydrogel® guard-Ultrahydrogel® 2000-Ultrahydrogel® Linear columns connected in series.

Samples run were quantified against a standard curve comprising of traceable standards from the American Polymer Standards Corporation: DXT3755K (peak molecular weight=2164 kDa), DXT820K (peak molecular weight=745 kDa), DXT760K (peak molecular weight=621 kDa), DXT670K (peak molecular weight=401 kDa), DXT530K (peak molecular weight=490 kDa), DXT500K (peak molecular weight=390 kDa), DXT270K (peak molecular weight=196 kDa), DXT225K (peak molecular weight=213 kDa), DXT150K (peak molecular weight=124 kDa), DXT55K (peak molecular weight=50 kDa), DXT50K (peak molecular weight=44 kDa) and DXT5K (peak molecular weight=4 kDa), the peak molecular weights of these standards being between about 4 kDa and about 2,200 kDa. The standard curve used may, for example, include Dextran 3755 kDa, at least one of Dextran 50 kDa and Dextran 55 kDa, and between 3 to 6 additional traceable standards discussed herein, the calibration points being the peak molecular weights of the calibrants used. An example calibration curve may consist of DXT3755K, DXT 820K, DXT530K, DXT500K, DXT225K and DXT55K. The columns used herein had a total effective molecular weight range that encompassed and extended beyond the peak molecular weight range of the standards used for quantification of the fucans.

A molecular weight stated for a fucan/fucoidan polymer herein is a value of molecular weight about which there will always be a distribution of molecules of higher and lower molecular weights, increasing or decreasing in amount or percentage as the molecular weight increases or decreases away from the specified molecular weight. The distribution may, but is not required to, have a generally Gaussian or distorted Gaussian shape.

Results in the tables herein contain abbreviations used for certain characteristics of a molecular weight distribution. Gel permeation chromatography is denoted by GPC, peak retention time is denoted by PRT, peak molecular weight is denoted by PMW, weight average molecular weight is denoted by WAMW, number average molecular weight is denoted by NAMW, percentage distribution is denoted by % dist., molecular weight is denoted by MW, polydispersity index is denoted by PDI and molecular weight cutoff is denoted by MWCO.

The following paragraphs turn to a brief general discussion of some methodologies that can be used to create the fucan-low endotoxin composition herein.

Modified Tangential Flow Filtration

A starting fucan composition, which can be a feedstock fucan composition, containing high levels of endotoxin undergoes a modified tangential flow filtration. The methods can comprise: subjecting the starting fucan composition plus a disrupting agent that disrupts cells and endotoxin aggregation to tangential flow filtration (TFF) across a first tangential flow filtration filter to produce a first retentate fucan composition. The disrupting agent can be, for example, one or more of sodium dodecyl sulfate (SDS), benzalkonium chloride, Triton® X 100, Triton® X 114, or sodium deoxycholate. The first retentate fucan composition is then subjected to tangential flow filtration with a secondary diafiltration solution across a second tangential flow filtration filter to remove residual disrupting agent from the retentate fucan composition, producing a second retentate fucan composition comprising the desired fucan-low endotoxin composition. If desired, the same TFF filter may be employed in both the first and second diafiltration processes.

The methods, systems, etc., herein may comprise pre-filtering the starting fucan composition in solution through a pre-filter to remove undesired particulate material. The disrupting agent may comprise an anionic detergent, a cationic detergent and/or a non-ionic detergent, for example, sodium dodecyl sulfate (SDS), benzalkonium chloride, Triton® X 100, Triton® X 114 and/or sodium deoxycholate.

Further embodiments include treating the first retentate fucan composition with a precipitating agent to produce A) a precipitate of the disrupting agent and B) a retentate-supernatant fucan composition. The supernatant fucan composition can then be subjected to additional tangential flow filtration to remove the residual disrupting agent from the supernatant fucan composition, producing a second retentate fucan composition comprising the desired fucan-low endotoxin composition. Treating the first retentate fucan composition with a precipitating agent may comprise treating the first retentate fucan composition with a salt and/or a base. In certain embodiments, the salt may be a chloride, bromide, iodide, fluoride, sulfate, sulfite, carbonate, bicarbonate, phosphate, nitrate, nitrite, acetate, citrate, silicate and/or cyanide of an alkali metal, alkali earth metal, aluminum and/or ammonium. In certain embodiments, the base may be a hydroxide and/or oxide of an alkali metal, alkali earth metal, aluminum and/or ammonium. In certain embodiments, the salt may be one of potassium chloride, potassium hydroxide, calcium chloride, barium chloride or calcium carbonate. The supernatant fucan composition can also be, if desired, pre-filtered to remove undesired particulate material.

The methods, systems, etc., can also comprise adding a bacteriostatic agent, for example to the starting fucan composition plus disrupting agent. The bacteriostatic agent can be, for example, at least one of ethylenediamine-tetraacetic acid (EDTA), 2,3-dimercapto-1-propanol, ethylene diamine, porphine or citric acid.

In some embodiments, the starting fucan composition may be provided as a solution. The starting fucan composition may have a fucan concentration in solution of greater than 0.1% w/v and less than 30% w/v. The disrupting agent may have a concentration in solution of greater than 0.1% w/v and less than 60% w/v. Impurities that may be removed by the above methods include without limitation particulates, lipids, fatty acids, phlorotannins, laminarins, alginates, proteins, Maillard reaction products, fucoxanthin, chlorophyll, free ions, bacteria, viruses, yeasts, molds, parasites, DNA and endotoxins.

FIG. 1 shows schematically an exemplary modified tangential flow filtration (TFF) system 1000 for obtaining a reduction in the impurity level of a starting fucan composition. A starting fucan composition in solution is supplied via input supply line 1002 to fucan container 1016. The starting fucan composition in a suitable solvent may be pre-filtered through pre-filter 1004, for example to remove undesired particulate matter.

TFF input pump 1014 pumps starting fucan composition to TFF filter 1010 via TFF supply line 1012. TFF filter 1010 can be supplied as a cassette designed to allow an input fluid supplied to it to pass over its filter on its retentate side, while allowing a permeate to exit via one or more output lines and treated input fluid to leave as retentate via another output line. TFF input pump 1014 provides a desired level of pressure over TFF filter 1010 between its retentate and permeate sides. In FIG. 1, the retentate of TFF filter 1010 is returned to fucan container 1016 via TFF retentate return line 1018 and TFF retentate valve 1017, while permeate is produced via TFF permeate output line 1019 for use outside of modified TFF system 1000 or to be discarded.

Before or while TFF input pump 1014 recirculates the starting fucan composition over TFF filter 1010, a disrupting agent, for example one of sodium dodecyl sulfate (SDS), benzalkonium chloride, Triton® X 100, Triton® X 114 or sodium deoxycholate, may be added to the starting fucan composition in fucan container 1016 from first diafiltration solution container 1020 via first diafiltration solution supply line 1025. The solution containing the first disrupting agent, being the first diafiltration solution, is used both to replenish solvent lost via the permeate on TFF permeate output line 1019 and/or to ensure that a predetermined number of diavolumes of starting fucan composition and disrupting agent are circulated over the TFF filter 1010. By controlling first diafiltration solution valve 1024, the disrupting agent may be added in a pulse process if desired. In other embodiments, the disrupting agent may be added in a continuous mode.

The number of diavolumes of disrupting agent to process over TFF filter 1010 may be predetermined. The process may be continued for a predetermined period of time, for a predetermined number of diavolumes of the disrupting agent, or until a predetermined purity level is achieved, for example the impurity level in the fucan container 1016 may be measured and the TFF process terminated when a suitably low impurity level has been attained. The impurity level measured may be the endotoxin level. The diafiltration of the starting fucan composition in solution across TFF filter 1010 with the first diafiltration solution provides a low endotoxin first retentate fucan composition in solution.

The residual disrupting agent can be removed from the low endotoxin first retentate fucan composition. This may be done by shutting first diafiltration solution valve 1024, TFF system output valve 1006, and allowing a suitable secondary diafiltration solution from second diafiltration solution container 1030 to enter fucan container 1016 via second diafiltration solution supply line 1035 and second diafiltration solution valve 1034. The mix in fucan container 1016 can then be subjected to TFF across TFF filter 1010 as before, for example via TFF supply line 1012, TFF input pump 1014, TFF retentate return line 1018, and TFF retentate valve 1017, or via other TFF filtration as may be desired.

The secondary diafiltration solution can be used, for example, both to replenish solvent lost via the permeate on TFF permeate output line 1019 and/or to ensure that a predetermined number of diavolumes of the first retentate fucan composition and secondary diafiltration solution are circulated over the TFF filter 1010. By controlling second diafiltration solution valve 1034, the secondary diafiltration solution may be added, e.g., in a pulse process and/or in a continuous mode. The number of diavolumes of secondary diafiltration solution to process over TFF filter 1010 may be predetermined. The process may be continued for a predetermined period of time, for a predetermined number of diavolumes of the secondary diafiltration solution, or the residual disruptive agent concentration in the fucan container 1016 may be measured and the TFF process terminated when a suitably low residual disruptive agent concentration has been attained. The resulting second retentate fucan composition in fucan container 1016 comprises the fucan-low endotoxin composition product of the modified TFF system 1000.

In some embodiments, the first retentate fucan composition in fucan container 1016 may be collected via assisted TFF system output line 1008 controlled by TFF system output valve 1006 for other intermediate treatment before being returned to fucan container 1016 for the secondary diafiltration solution treatment discussed herein after the intermediate treatment. In one example of an intermediate treatment, the first retentate fucan composition from fucan container 1016 may be treated with a precipitating agent and the resulting mix subjected to centrifugation in order to separate the desired supernatant fucan composition from the precipitate. By way of example, if the disrupting agent is sodium dodecyl sulfate, then the precipitating agent may be for example potassium chloride and potassium hydroxide. Sodium dodecyl sulfate in particular, while having significant benefits, is a difficult substance to remove from the low endotoxin first retentate fucan composition in fucan container 1016 and precipitation in an intermediate process step aids in this removal. After the intermediate step, the supernatant of the intermediate step may be returned to fucan container 1016 and subjected to the secondary diafiltration solution TFF step as already discussed. In the case of the disrupting agent being sodium dodecyl sulfate, this second TFF step seeks to remove remnants of the sodium dodecyl sulfate that remained in the supernatant fucan composition after the intermediate precipitation and centrifugation steps.

Solid Phase Extraction

A fucan composition such as a starting fucan composition containing high levels of endotoxin is subjected to a solid phase extraction. The methods can comprise: providing in solid form a starting fucan composition comprising endotoxins among other impurities and an extraction media incapable of dissolving fucans, configured for dissolving impurities; mixing the starting fucan composition with the extraction media to form a mixture of the undissolved solid fucan composition and the extraction media, the extraction media containing dissolved endotoxins and possibly other impurities; separating the fucan-low endotoxin composition as an undissolved solid fucan composition from the extraction media containing dissolved endotoxins among other impurities; and collecting the fucan-low endotoxin composition as a solid after removing the fucan-low endotoxin composition from the extraction media. The separating may comprise one or more of, for example, centrifugation, filtration, sedimentation and hydrodynamic fluid separation.

The extraction media can comprise, for example, one or more of a base, a detergent and an oxidizing agent. Suitable extraction media that do not dissolve the fucan include organic solvents with a relative polarity less than 0.765, for example, ethanol, isopropanol, methanol, benzene, diethyl ether, decamethylcyclo-pentasiloxane, ethyl acetate, butanol, hexane, heptane, heptanol, octanol and decanol. Suitable bases include without limitation sodium hydroxide, potassium hydroxide, lithium hydroxide, and calcium hydroxide. Suitable oxidizing agents include without limitation one or more of hydrogen peroxide, urea peroxide, and oxidizing bleaches, including sodium hypochlorite. Suitable detergents include without limitation nonionic surfactants, for example the Tween®, Brij® and Triton® ranges of detergents; anionic surfactants, for example sodium dodecyl sulfate (SDS), sodium deoxycholate; and cationic surfactants, for example benzalkomium chloride (BAC). Particular fucans lending themselves to the methods herein include, but are not limited to fucoidan. The treating of the original, e.g., starting fucan composition with the extraction media may extend from one minute to 120 hours.

The methods may further comprise desalting the starting fucan composition before providing in solid form the starting fucan composition. The desalting may comprise diafiltrating the starting fucan composition as a solution in water across a molecular weight cutoff (MWCO) tangential flow filtration (TFF) filter. The diafiltrating may comprise diafiltrating the starting fucan composition with distilled water. The molecular weight cutoff TFF filter can have a molecular weight cutoff smaller than a desired molecular weight separation point or target in or for the fucan-low endotoxin composition, for example a 50 kDa, 70 kDa, 100 kDa, 200 kDa, 300 kDa, 500 kDa or 1000 kDa molecular weight cut-off. The diafiltrating may further comprise pre-filtering the starting fucan composition through a suitable pre-filter to remove particulate matter. The methods may further comprise lyophilizing and/or spray-drying a suitable starting fucan composition in solution prior to providing in solid form the starting fucan composition. The methods may further comprise precipitating from a solution a suitable starting fucan composition prior to providing in solid form the starting fucan composition. Suitable precipitants include without limitation ethanol, isopropanol, propanol, acetone, methanol, dimethyl sulfoxide, dimethyl formamide, ethylene glycol, tetrahydrofuran, acetonitrile, glyme, diglyme, dioxane, the solubility of the fucan decreasing as the polarity of the precipitating fluid decreases. Impurities that may be removed by the above method include without limitation particulates, lipids, fatty acids, phlorotannins, laminarins, alginates, proteins, Maillard reaction products, fucoxanthin, chlorophyll, free ions, bacteria, viruses, yeasts, molds, parasites, DNA and endotoxins.

Chemically Induced Precipitation

A starting fucan composition, or other suitable fucan compositions, containing high levels of endotoxins and other impurities, for example suspended particulates, undergoes a chemically-induced precipitation of impurities. In certain embodiments, the methods can comprise: providing a starting fucan composition in a starting solution; precipitating impurities from the starting solution by means of an ionic-multivalent impurity precipitant to provide a mixture of suspended impurities, precipitated impurities and supernatant; separating the suspended impurities and precipitated impurities from the supernatant solution; and collecting the supernatant solution comprising the desired fucan-low endotoxin composition after separating the suspended impurities and precipitated impurities from the supernatant.

Suitable impurity precipitants include ionic-multivalent salts and/or bases of divalent and trivalent cations. Examples of such suitable salts include without limitation chlorides, bromides, iodides, fluorides, sulfates, sulfites, carbonates, bicarbonates, phosphates, nitrates, nitrites, acetates, citrates, silicates and/or cyanides of alkaline earth metals, zinc, aluminum, copper and iron. Examples of such suitable bases include without limitation hydroxides and/or oxides of alkaline earth metals, zinc, aluminum, copper and/or iron. Separating the suspended impurities and precipitated impurities from the supernatant solution may comprise flocculating impurities in the mixture. Suitable flocculants include without limitation potassium aluminum sulfate; sodium aluminum sulfate; ammonium aluminum sulfate; calcium chloride; sodium phosphate; aluminum hydroxide; aluminum chloride; ferric chloride; ferric sulfate; ferrous sulfate; sodium silicate; calcium silicate; calcium phosphate; zinc chloride; calcium carbonate; calcium bicarbonate; potassium sulfate; magnesium phosphate; acrylamides; acrylic acid; aluminum chlorohydate; polyaluminium chloride; tannins; formaldehyde; melamine; N,N-dimethylaminocthyl acrylate methyl chloride; N,N-dimethylaminoethyl methacrylate methyl chloride quaternary; and polydiallyldimethyl-ammonium chloride. As may be seen from the foregoing list of flocculants, in some embodiments, the flocculant may be the impurity precipitant. Separating the precipitated, suspended and/or flocculated impurities from the supernatant solution may comprise at least one of centrifuging, filtering, sedimentation and hydrodynamic flow separation of the mixture of impurities and the supernatant solution.

The methods may further comprise desalting the starting fucan composition before providing the starting fucan composition. The desalting may comprise diafiltrating the starting fucan composition as an aqueous solution across a TFF filter. The diafiltrating may comprise diafiltrating the starting fucan composition with distilled water. The diafiltrating may comprise diafiltrating the starting fucan composition across a TFF filter with a molecular weight cutoff (MWCO) of 5 kDa, 10 kDa, 30 kDa, 50 kDa, 70 kDa or 100 kDa. The diafiltrating may further comprise pre-filtering the starting fucan composition in through a suitable pre-filter to remove particulate matter.

The methods may further comprise maintaining a pH of between about 7 and 14 to inhibit or prevent degradation of fucans in acidic environments. Maintaining the pH between about 7 and 14 may comprise the addition of a suitable base, for example, sodium hydroxide. A suitable base may be added to the starting fucan composition before precipitating impurities from the solution by means of an ionic-multivalent impurity precipitant. In other embodiments, a suitable base may be added to the mixture of precipitated impurities and supernatant solution after precipitating impurities from the solution by means of an ionic-multivalent impurity precipitant. In yet other embodiments, a suitable base may be added to the supernatant solution after separating the suspended impurities and precipitated impurities from the supernatant solution.

Example fucans suitable for treatment by the above methods include without limitation fucoidan, and the concentration of the fucan in solution may be between 0.01% w/v and 50% w/v. Impurities that may be removed by the above method include without limitation particulates, lipids, fatty acids, phlorotannins, laminarins, alginates, proteins, Maillard reaction products, fucoxanthin, chlorophyll, free ions, bacteria, viruses, yeasts, molds, parasites, DNA and endotoxins.

Lysis and Flocculation

A starting fucan composition, such as a feedstock fucan composition, containing high levels of endotoxin undergoes lysis and flocculation. The methods in this example can comprise: providing a starting fucan composition; rendering the starting fucan composition alkaline; adding to the starting fucan composition a cellular disrupting agent to produce a reaction mixture, the cellular disrupting agent lysing cellular components in the starting fucan composition and releasing into the alkaline reaction mixture lysates comprising biomolecular components; removing from the reaction mixture the cellular disrupting agent and at least a portion of the impurities to leave undegraded the desired fucan-low endotoxin composition.

The removing of the cellular disrupting agent may comprise any one or more of precipitation, flocculation, tangential flow filtration, micellar phase separation, ionic adsorption, and hydrophobic adsorption. The removal of impurities may comprise any one or more of precipitation, flocculation, tangential flow filtration, micellar phase separation, ionic adsorption, and hydrophobic adsorption. Any of these removal methods or combinations of removal methods may comprise centrifuging, filtering, sedimentation or hydrodynamic flow separation of any mixture of solid and liquid phases.

Suitable cellular disrupting agents include without limitation anionic, non-ionic and cationic detergents, for example sodium dodecyl sulfate (SDS), benzalkonium chloride, Triton X 100®, Triton X 114®, Brij® detergents, Tween® detergents, sodium deoxycholate, and alkylbenzenesulfonates.

In one embodiment of the methods, the cellular disrupting agent is sodium dodecyl sulfate (SDS) and the removing of the cellular disrupting agent comprises adding a precipitant for rendering the cellular disrupting agent insoluble in the alkaline reaction mixture and to thereby precipitate the cellular disrupting agent. In this embodiment, the removing of the cellular disrupting agent may further comprise adding a flocculant to the reaction mixture to flocculate the precipitated cellular disrupting agent and along with it at least a portion of the impurities. The removing of the cellular disrupting agent may further comprise centrifuging after the flocculation.

Suitable precipitants for sodium dodecyl sulfate and alkylbenzenesulfonates include without limitation potassium hydroxide, potassium chloride, calcium chloride, calcium carbonate and barium chloride. Suitable flocculants include without limitation potassium aluminum sulfate; sodium aluminum sulfate; ammonium aluminum sulfate; calcium chloride; sodium phosphate; aluminum hydroxide; aluminum chloride; ferric chloride; ferric sulfate; ferrous sulfate; sodium silicate; calcium silicate; calcium phosphate; zinc chloride; calcium carbonate; calcium bicarbonate; potassium sulfate; magnesium phosphate; acrylamides; acrylic acid; aluminum chlorohydate; polyaluminium chloride; tannins; formaldehyde; melamine; N,N-dimethylaminoethyl acrylate methyl chloride; N,N-dimethylaminoethyl methacrylate methyl chloride quaternary; and polydiallyldimethyl-ammonium chloride.

It is to be understood hereby that the cellular disrupting agent may undergo a change in the process of precipitation. For example, if the cellular disrupting agent is sodium dodecyl sulfate (SDS), the precipitant may be potassium hydroxide (KOH) and the sodium cation may be replaced as part of the precipitation process by potassium, the resulting potassium dodecyl sulfate being insoluble in the reaction mixture and thereby precipitating. The dodecyl sulfate cation, which functionally is the cellular disrupting portion of the SDS, stays intact in this process.

In yet other embodiments of the methods, the cellular disrupting agent may be one or more of sodium dodecyl sulfate (SDS) and sodium deoxycholate and the removing of the cellular disrupting agent comprises anionic adsorption. The anionic adsorption may comprise adding a suitable positively charged adsorbent for a suitable amount of time, followed by the removal of the adsorbent. The anionic adsorption may further comprise flowing the reaction mixture over a column or filter packed with a suitable positively charged adsorbent at a suitable flow rate.

In yet other embodiments of the methods, the cellular disrupting agent may be benzalkonium chloride and the removing of the cellular disrupting agent comprises cationic adsorption. The cationic adsorption may comprise adding a suitable negatively charged adsorbent for a suitable amount of time, followed by the removal of the adsorbent. The cationic adsorption may further comprise flowing the reaction mixture over a column or filter packed with a suitable negatively charged adsorbent at a suitable flow rate.

In yet other embodiments of the methods, the cellular disrupting agent may be one or more of Triton X 100®, Triton X 114®, Brij® and Tween® detergents and the removing of the cellular disrupting agent comprises micellar phase separation. The micellar phase separation may comprise altering the temperature of the reaction mixture such that the temperature of the reaction mixture exceeds the cloud point of the cellular disrupting agent. The micellar phase separation may comprise centrifuging the reaction mixture to obtain the desired phase separation.

In further embodiments of methods, the cellular disrupting agent may be any one or more of sodium dodecyl sulfate (SDS), benzalkonium chloride, Triton X 100®, Triton X 114®, Brij® detergents, Tween® detergents, sodium deoxycholate, and alkylbenzenesulfonates, and the and the removing of the cellular disrupting agent comprises one or more of hydrophobic adsorption and a combination of dilution and tangential flow filtration (TFF). The hydrophobic adsorption may comprise adding a suitable hydrophobic adsorbent for a suitable amount of time, followed by the removal of the adsorbent. The hydrophobic adsorption may comprise flowing the reaction mixture over a column or filter packed with a suitable hydrophobic adsorbent at a suitable flow rate. The removal by dilution and TFF may comprise diluting the reaction mixture such that the cellular disrupting agent falls below its critical micellar concentration and thus can be removed by means of tangential flow filtration over a suitable molecular weight cut-off (MWCO) TFF filter that allows for the permeation of the cellular disrupting agent from a fucan containing retentate. The removal by dilution and TFF may involve diafiltering the reaction mixture over the TFF filter with a suitable number of diavolumes.

The methods may further comprise adding a chelating agent to the reaction mixture to chelate free multivalent cations in the reaction mixture. The chelating agent may be added after providing the starting fucan composition and before the removing of the cellular disrupting agent. The methods may further comprise quenching oxidants in the reaction mixture. The quenching of oxidants may comprise adding an oxidant-quenching agent to the reaction mixture before or after the removing of the cellular disrupting agent.

The methods may comprise adding a bacteriostatic agent to the reaction mixture. The bacteriostatic agent may be added after providing the starting fucan composition and before the removing of the cellular disrupting agent. Suitable bacteriostatic agents include without limitation sodium sulfite, ethylenediaminetetraacetic acid (EDTA), benzalkonium chloride, ethanol, and thiourea.

Suitable chelating agents include without limitation ethylenediaminetetraacetic acid (EDTA), 2,3-dimercapto-1-propanol, ethylene diamine, porphine and citric acid. Suitable oxidant-quenching agents include without limitation sulfite, nitrite and phosphite salts. As is evident from the above, several of the compounds listed may have more than one function in the methods.

Suitable hydrophobic adsorbents include without limitation activated carbon, diatomaceous earth, acrylic ester non-ionic resins, polystyrene non-ionic resins, styrene-divinylbenzene (DVB) non-ionic resins. Suitable anionic adsorbents include without limitation: amine functionalized styrene-DVB resins, amine functionalized methacrylate resins, amine functionalized methyl methacrylate resins, amine functionalized butyl methacrylate resins, amine functionalized agarose resins, amine functionalized dextran resins, amine functionalized ceramic based resins, amine functionalized silicates, and lipid removal agent (LRA).

In some embodiments, the starting fucan composition may be provided as a solution. Example fucans suitable for treatment by the above method include without limitation fucoidan. The starting fucan composition may have a fucan concentration in solution of greater than 0.1% w/v and less than 30% w/v. The cellular disrupting agent may have a concentration in solution of greater than 0.1% w/v and less than 60% w/v. Impurities that may be removed by the above method include without limitation particulates, lipids, fatty acids, phlorotannins, laminarins, alginates, proteins, Maillard reaction products, fucoxanthin, chlorophyll, free ions, bacteria, viruses, yeasts, molds, parasites, DNA and endotoxins.

Anionic Adsorption

A starting fucan composition or other desired fucan composition containing high levels of endotoxin undergoes anionic adsorption. The methods can comprise: subjecting the starting fucan composition to anion exchange with an anion-exchange macroporous resin in an anion exchange system to produce a fucan-low endotoxin composition with a substantially lower endotoxin level than the starting fucan composition, and collecting the fucan-low endotoxin composition as an output of the anion exchange system. The methods can comprise subjecting the starting fucan composition to anion exchange with an anion-exchange macroporous resin having a pore size greater than the average hydrodynamic size of undesired endotoxins in the starting fucan composition. The methods can comprise pre-treating the starting fucan composition with a disrupting agent.

The methods may further comprise desalting the starting fucan composition before subjecting the starting fucan composition to anion exchange. The desalting may comprise diafiltrating the starting fucan composition in solution across a molecular weight cutoff (MWCO) TFF filter. The MWCO TFF filter can have a molecular weight cutoff smaller than a desired molecular weight separation point or target in or for the fucan-low endotoxin composition, for example a 5 kDa, 10 kDa, 30 kDa, 50 kDa, 70 kDa, 100 kDa, 200 kDa, 300 kDa, 500 kDa or 1000 kDa molecular weight cut-off. The diafiltrating may further comprise pre-filtering the starting fucan composition in through a suitable pre-filter to remove particulate matter.

The methods may comprise adjusting the ratio of the starting fucan composition to macroporous anion-exchange resin to a predetermined ratio. The predetermined ratio may be between 1:100 and 10:1, between 1:90 and 1:1, 1:80 and 1:5 or between 1:70 and 1:10 starting fucan composition: macroporous anion exchange resin. In some embodiments, the predetermined ratio may be based on mass of the starting fucan composition and of the macroporous anion exchange resin.

The methods, systems, etc., may comprise subjecting the starting fucan composition to anion exchange with the resin for a predetermined period of time. The predetermined period of time may be between about 5 minutes and 300 hours, for example about 10 minutes, 30 minutes and 1, 2, 3, 5, 10, 30, 100 and 300 hours.

The methods, systems, etc., may comprise subjecting the starting fucan composition to anion exchange with a strong base macroporous anion-exchange resin, a weak base macroporous anion-exchange resin or a macroporous mixed charge resin. “Strong base” and “weak base” are used according to their ordinary meanings, for example a “strong base” being a resin that does not lose charge under any typical ion-exchange circumstances, for example a quaternary amine functionalized resin, and a weak base being a resin that does lose charge under high pH conditions, for example, a primary, secondary or tertiary amine functionalized resin.

The methods, systems, etc., may comprise subjecting the starting fucan composition to anion exchange with a macroporous resin comprising at least one of primary, secondary, tertiary and quaternary amino groups. The primary amino groups may be amine groups. The secondary amino groups may be at least one of, for example, benzylamine groups and dimethyl amino groups. The tertiary amino groups may be at least one of, for example, diethylaminoethyl groups and dimethylaminoethyl groups. The quaternary amino groups may be for example trimethyl ammonium groups and triethyl ammonium groups. The resin may comprise, but is not limited to, one or more of styrene, agarose, dextran, acrylate, methacrylate, methyl methacrylate, butyl methacrylate, divinylbenzene, cellulose, silica, and ceramic.

The methods, systems, etc., may comprise using an ion exchange resin having an average pore size between about 5 nm and about 1000 nm, for example about 5 nm, 10 nm, 15 nm, 20 nm, 25 nm, 30 nm, 40 nm, 50 nm, 60 nm, 80 nm, 100 nm, 200 nm, 300 nm, 400 nm, 500 nm, 750 nm or 1000 nm The ion exchange resin can have an exclusion limit of between about 5 kDa or 50 kDa and 50,000 kDa, for example about 50 kDa, 100 kDa, 200 kDa, 500 kDa, 1,000 kDa, 2,000 kDa, 3,000 kDa, 4,000 kDa, 5,000 kDa, 6,000 kDa, 8,000 kDa, 9,000 kDa 10,000 kDa, 20,000 kDa, 40,000 kDa or 50,000 kDa. In some embodiments, the exclusion limit is based on the size of globular proteins.

Figure 2:
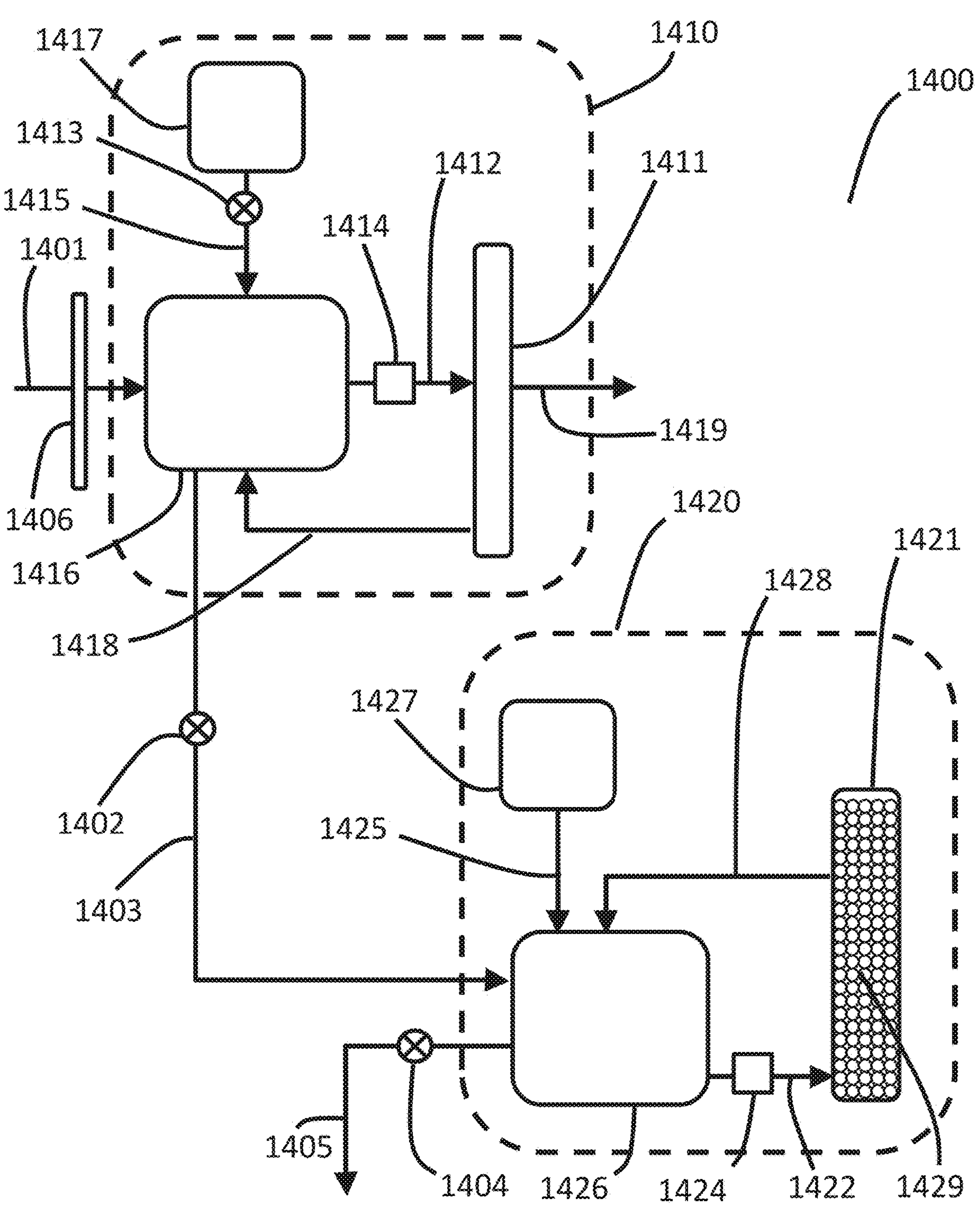
FIG. 2 schematically depicts a system for obtaining a desired reduction in endotoxin level in a starting fucan composition using anion absorption.

The system in FIG. 2 depicts an exemplary apparatus for an anionic adsorption endotoxin removal system 1400 for the removal of endotoxins from a starting fucan composition. A solution containing the starting fucan composition is supplied via input supply line 1401 to tangential flow filtration (TFF) subsystem fucan container 1416. The starting fucan composition in a suitable solvent may be pre-filtered through pre-filter 1406 to remove undesired particulate matter. In a desalting process, TFF subsystem pump 1414 pumps the starting fucan composition to TFF filter 1411 of TFF subsystem 1410 via TFF filter supply line 1412.

TFF filter 1411 can be supplied as a cassette designed to allow an input fluid supplied to it to pass over its filter on its retentate side, while allowing a permeate to exit via a first output line and treated input fluid to leave as retentate via another output line. For the present exemplary methods, the MWCO of TFF filter 1411 is chosen to allow permeation of salt components while retaining the fucan in the retentate for subsequent anion adsorption treatment in anion exchange subsystem 1420. TFF subsystem pump 1414 provides a level of pressure over TFF filter 1411 between its retentate and permeate sides. In FIG. 2, the retentate of TFF filter 1411 is returned to TFF subsystem fucan container 1416 via TFF subsystem retentate return line 1418, while permeate containing the unwanted salt components of the starting fucan composition is produced via TFF subsystem permeate output line 1419 for use outside anionic adsorption endotoxin removal system 1400 or to be discarded.

While TFF subsystem pump 1414 recirculates the starting fucan composition and retentate over TFF filter 1411, deionized water or a low conductivity solution from TFF subsystem diafiltration solution container 1417 may be supplied via TFF subsystem diafiltration solution supply line 1415. The diafiltration solution is used to replenish retentate solution lost via the permeate on TFF subsystem permeate output line 1419 and/or to ensure that a predetermined number of diavolumes of input starting fucan and diafiltration solution are circulated over TFF filter 1411. By controlling diafiltration solution valve 1413, flush solution may be added in a pulse and/or continuous process. The number of diavolumes of flush solution to process over TFF filter 1411 may be predetermined. In some embodiments, the flush solution may be deionized water.

Inter-subsystem valve 1402 may be shut during the above processing, and retentate of TFF filter 1411 of TFF subsystem 1410 collected into a container (not shown) before being supplied to anion exchange subsystem fucan container 1426 of anion exchange subsystem 1420. The collected retentate may be supplied to anion exchange subsystem fucan container 1426 of anion exchange subsystem 1420 via a TFF subsystem retentate output line 1403. In other embodiments, the collected retentate may be transferred in a container (not shown) to anion exchange subsystem fucan container 1426. In yet other embodiments of the system, the inter-subsystem valve 1402 may be maintained open and the retentate of TFF filter 1411 may be supplied via TFF subsystem retentate output line 1403 on a continuous basis to anion exchange subsystem fucan container 1426. The retentate supplied to anion exchange subsystem 1420 can have a lower salt content than the starting fucan composition. The reduction in salt content of the starting fucan composition may be desired for subsequent processing in anion exchange subsystem 1420. In some embodiments, the starting fucan composition can be provided as a desalted starting fucan composition, and the processing through TFF subsystem 1410 can be bypassed.

Anion exchange vessel 1421 of anion exchange subsystem 1420 contains a volume of macroporous anion exchange resin 1429. The pore size of the macroporous anion exchange resin 1429 is chosen to preferentially adsorb endotoxin molecules while leaving behind fucan molecules. Such resin can comprise substantially spherical particles of styrene crosslinked with divinylbenzene and having pores containing quaternary ammonium groups. The endotoxin, whether as individual molecules, clusters of molecules, or micelles, can be preferentially adsorbed into the pores of the resin based on the hydrodynamic size of the endotoxin molecules, clusters, or micelles in solution. In an anion exchange process, an anion exchange subsystem pump 1424 pumps the retentate fucan composition to anion exchange vessel 1421 of anion exchange subsystem 1420 via anion exchange vessel supply line 1422.

The anion exchange subsystem output valve 1404 may be closed during the processing of the retentate fucan composition from TFF subsystem 1410 in anion exchange vessel 1421. Solution flowing through the anion exchange vessel 1421 is returned to anion exchange subsystem fucan container 1426 via anion exchange vessel output line 1428, resulting in the recirculation of the solution. During the recirculation, the macroporous anion exchange resin 1429 adsorbs the endotoxin from the retentate fucan composition.

The endotoxin level in anion exchange subsystem fucan container 1426 may be measured or monitored. When the solution has been recirculated for a suitable period of time, or when it has attained a predetermined desired endotoxin level, anion exchange subsystem output valve 1404 may be opened to output a fucan-low endotoxin composition via anion exchange subsystem output line 1405.

Turning to disrupting agent container 1427 and disrupting agent supply line 1425 of FIG. 2, in such embodiments a disrupting agent is added from disrupting agent container 1427 via disrupting agent supply line 1425. The disrupting agent may disrupt clusters or micelles of the endotoxins, making the resulting molecules more readily adsorbable within the pores of the macroporous anion exchange resin 1429. In certain embodiments, the retentate of TFF filter 1411 may be treated with the disrupting agent. Suitable disrupting agents include but are not limited to Triton® X100, Triton® X114, Brij® 35, Tween® 20 and benzalkonium chloride.

Liquid-Liquid Extraction

A starting fucan composition, such as a feedstock fucan composition, containing high levels of endotoxin undergoes liquid-liquid extraction. The methods can comprise: providing the starting fucan composition in an aqueous starting solution; mixing the starting solution with an organic solvent to obtain an aqueous-organic phase mixture having an aqueous portion comprising a fucan-low endotoxin composition, and an organic portion comprising hydrophobic impurities including endotoxins; separating the aqueous portion from the organic portion; and collecting the aqueous portion comprising the fucan-low endotoxin composition.

The methods may further comprise desalting the starting fucan composition before mixing with the aqueous starting solution an organic solvent. The desalting may comprise diafiltrating the starting fucan composition as a solution in water across a molecular weight cutoff (MWCO) tangential flow filtration (TFF) filter. The diafiltrating may comprise diafiltrating the starting fucan composition with distilled water. The molecular weight cutoff TFF filter can have a molecular weight cutoff smaller than a desired molecular weight separation point or target in or for the fucan-low endotoxin composition, for example a 5 kDa, 10 kDa, 30 kDa, 50 kDa, 70 kDa, 100 kDa, 200 kDa, 300 kDa, 500 kDa or 1000 kDa molecular weight cut-off. The diafiltrating may further comprise pre-filtering the starting fucan composition in through a suitable pre-filter to remove particulate matter.

Mixing the aqueous starting solution with an organic solvent may comprise shaking the aqueous-organic phase mixture, stirring the aqueous-organic phase mixture, exposing the aqueous-organic phase mixture to high-shear, recirculating the aqueous portion into the organic portion and recirculating the organic portion into the aqueous portion.

Separating the aqueous portion from the organic portion may comprise at least one of centrifugation, decanting, separatory funnel separation and hydrodynamic flow separation.

Suitable organic solvents for use with this method include organic solvents with a relative polarity less than 0.765, for example, ethanol, isopropanol, methanol, benzene, decamethylcyclo-pentasiloxane, ethyl acetate, hexane, heptanol, octanol, decanol, heptane, isobutyl acetate, anisole, isopropyl acetate, 1-butanol, butyl acetate, methylisobutylketone, pentane, 1-pentanol, ethyl ether, and propyl acetate. The organic phase may contain impurities, for example, lipids, fatty acids, phlorotannin, proteins, fucoxanthin, chlorophyll, and/or endotoxins.

Chemical Structural Modification

The methods, systems etc. discussed herein can comprise chemical structural modification of the fucan composition, particularly the fucans in the fucan composition. The chemical structural modification may involve removal of functional groups from the fucan, for example, O-acetyl, N-acetyl, methoxy, hydroxyl, carboxylic and/or sulfate functional groups from the fucan structure. The chemical structural modification may involve the use of a wide variety of chemical reagents, for example, acids, bases, detergents and/or oxidizing agents.

Diseases and Conditions

Fibrous Adhesions

A fibrous adhesion is a type of scar that forms between two parts of the body, usually after surgery (this type of fibrous adhesion may be referred to as a surgical adhesion). Fibrous adhesions can cause severe problems. For example, fibrous adhesions involving the female reproductive organs (ovaries, Fallopian tubes) can cause infertility, dyspareunia and severe pelvic pain. Fibrous adhesions that occur in the bowel can cause bowel obstruction or blockage, and fibrous adhesions can also form in other places such as around the heart, spine and in the hand. In addition to surgery, fibrous adhesions can be caused for example by endometriosis, infection, chemotherapy, radiation, trauma and cancer.

A variety of fibrous adhesions are discussed in this document. Terms such as surgical adhesions, post-surgical adhesions, postoperative adhesions, adhesions due to pelvic inflammatory disease, adhesions due to mechanical injury, adhesions due to radiation, adhesions due to radiation treatment, adhesions due to trauma, and adhesions due to presence of foreign material all refer to adherence of tissues to each other due to a similar mechanism and are all included in the term fibrous adhesions.

Fibrous adhesion formation is a complex process in which tissues that are normally separated in the body grow into each other. Surgical adhesions (also known as post-surgical adhesions) develop from the otherwise normal wound healing response of the tissues to trauma and have been reported to occur in over two-thirds of all abdominal surgical patients (Ellis, I I., *Surg. Gynecol. Obstet.* 133:497 (1971)). The consequences of these fibrous adhesions are varied and depend upon the surgical site or other site, such as a disease site, involved. Problems may include chronic pain, obstruction of the intestines and even an increased risk of death after cardiac surgery (diZerega, G. S., *Prog. Clin. Biol. Res.* 381:1-18 (1993); diZerega, G. S., *Fertil. Steril.* 61:219-235 (1994); Dobell, A. R., Jain, A. K., Ann. *Thorac. Surg.* 37:273-278 (1984)). In women of reproductive age, fibrous adhesions involving the uterus, fallopian tubes or ovaries are estimated to account for approximately 20% of all infertility cases (Holtz, G., Fertil. *Steril.* 41:497-507 (1984); Weibel, M. A. and Majno, G. *Am. J. Surg.* 126:345-353 (1973)).

The process of fibrous adhesion formation initially involves the establishment of a fibrin framework and normal tissue repair. The normal repair process allows for fibrinolysis alongside mesothelial repair. However, in fibrous adhesion formation the fibrin matrix matures as fibroblasts proliferate into the network and angiogenesis occurs resulting in the establishment of an organized fibrous adhesion within about 3 to 5 days (Buckman, R. F., et al., *J. Surg. Res.* 21:67-76 (1976); Raferty, A. T., *J. Anat.* 129:659-664 (1979)). Inflammatory processes include neutrophil activation in the traumatized tissues, fibrin deposition and bonding of adjacent tissues, macrophage invasion, fibroblast proliferation into the area, collagen deposition, angiogenesis and the establishment of permanent fibrous adhesion tissues.

Various attempts have been made to prevent surgical adhesions. These involve pharmacological approaches targeted at influencing the biochemical and cellular events that accompany surgical traumas well as barrier methods for the separation of affected tissues. For example, the use of peritoneal lavage, heparinized solutions, procoagulants, modification of surgical techniques such as the use of microscopic or laparoscopic surgical techniques, the elimination of talc from surgical gloves, the use of smaller sutures and the use of physical barriers (films, gels or solutions) aiming to minimize apposition of serosal surfaces, have all been attempted. Currently, preventive therapies also include prevention of fibrin deposition, reduction of inflammation (steroidal and non-steroidal anti-inflammatory drugs) and removal of fibrin deposits.

Interventional attempts to prevent the formation of post-surgical adhesions have included the use of hydroflotation techniques or barrier devices. Hydroflotation involves the instillation of large volumes of polymer solutions such as dextran (Adhesion Study Group, *Fertil. Steril.* 40:612-619 (1983)), or carboxymethyl cellulose (Elkins, T. E., et al., *Fertil. Steril.* 41:926-928 (1984)), into the surgical space in an attempt to keep the organs apart. Synthetic barrier membranes made from oxidized regenerated cellulose (e.g., Interceed™), polytetrafluoroethylene (Gore-tex surgical membrane) and fully resorbable membranes made from a modified hyaluronic acid/carboxymethylcellulose (HA/CMC) combination (Seprafilm™) have also been used to reduce post-surgical adhesion formation in both animals and humans (Burns, J. W., et al., *Eur. J. Surg. Suppl.* 577:40-48 (1997); Burns, J. W., et al., *Fertil. Steril.* 66:814-821 (1996); Becker, J. M., et al., *J. Am. Coll. Surg.* 183:297-306 (1996)). The success of these HA/CMC membranes may derive from their ability to provide tissue separation during the peritoneal wound repair process when fibrous adhesions form. The membranes were observed to form a clear viscous coating on the injured tissue for 3-5 days after application, a time period that is compatible with the time course of post-surgical adhesion formation (Ellis, H., Br. *J. Surg.* 50:10-16 (1963)). Unfortunately, limited success has been seen with these methods.

Peritonitis involves inflammation of the peritoneum. Peritonitis can cause severe problems. For example, abdominal pain, abdominal tenderness and abdominal guarding. Peritonitis may involve spontaneous, anatomic and/or peritoneal dialysis related inflammation. Peritonitis may involve an infection, for example, perforation of a hollow viscus, disruption of the peritoneum, spontaneous bacterial peritonitis, and systemic infections may result in infection and peritonitis. Peritonitis may also not involve an infection, for example, leakage of sterile body fluids into the peritoneum, and sterile abdominal surgery may result in peritonitis. Various attempts have been made to prevent and/or treat peritonitis. For example, general supportive measures such as intravenous rehydration, antibiotics, and surgery. There is an unmet need for compounds, compositions, methods and the like (including delivery approaches) to inhibit, or otherwise treat and/or prevent, peritonitis, preferably more effectively with few side effects.

The fucan-low endotoxin compositions discussed herein can be used to treat fibrous adhesions in a patient and can be included as a component of, or be, a fucan-low endotoxin medical composition, medical device, combination or pharmaceutical product configured and can be composed to treat fibrous adhesions. For example, a fucan-low endotoxin medical composition or medical device comprising between about 0.02 mg/mL to about 100 mg/mL, for example 0.1 mg/mL, 0.2 mg/mL, 0.3 mg/mL, 0.5 mg/mL, 0.9 mg/mL, 1 mg/mL, 2.5 mg/mL, 5 mg/mL 7.5 mg/mL, of a fucan-low endotoxin composition herein dissolved in a physiological salt solution. The physiological salt solution can be, for example, Lactated Ringer's Injection USP (LRS), normal saline and physiological Dextran solution.

The fucan-low endotoxin medical compositions and medical devices, which can be liquid medical compositions and devices, herein can contain pharmaceutically acceptable excipients such as buffers, stabilizers, preservatives, adjuvants, etc. Such fucan-low endotoxin medical compositions and medical devices can be used to treat fibrous adhesions pre-, during, or post-surgery by administering between about 0.01 mL/kg (per kilogram bodyweight of the patient or target) to about 10 mL/kg or 15 mL/kg of the fucan medical compositions or devices in the preceding paragraph. Doses and device quantities include, for example, about 0.03 ml/kg, 0.1 mL/kg, 0.2 ml/kg, 0.4 mL/kg, 0.5 mL/kg, 0.6 mL/kg, 1 mL/kg, 1.2 mL/kg, 2 mL/kg, 3 mL/kg, 4 mL/kg, 5 mL/kg, 8 mL/kg, 10 mL/kg and 15 mL/kg of the fucan-low endotoxin medical composition or medical device to the surgical site of the patient. In further embodiments, such fucan-low endotoxin medical compositions and medical devices can be used to treat fibrous adhesions at any selected target site, for example lesions, abrasions, injury sites, surgical sites and post-surgical sites by administering between about 0.04 mg/kg or 0.1 mg/kg to about 25 mg/kg or 50 mg/kg. Some examples of such doses include, for example, about 0.04 mg/kg, 0.075 mg/kg, 0.1 mg/kg, 0.2 mg/kg, 0.5 mg/kg, 1 mg/kg, 1.3 mg/kg, 1.5 mg/kg, 2 mg/kg, 3 mg/kg, 4 mg/kg, 5 mg/kg, 7.5 mg/kg, 8 mg/kg, 10 mg/kg, 15 mg/kg, 20 mg/kg, 25 mg/kg and 50 mg/kg of the fucans herein, including for example the fucan-low endotoxin compositions herein, to the surgical site of the patient. The administering can be accomplished, for example, by instilling a liquid medical composition or medical device generally throughout the target area; directing the liquid medical composition or medical device at a specific location(s) within the target area; spraying the liquid medical composition or medical device generally or at a specific location(s) within the target area; or, spraying or otherwise delivering the liquid medical composition or medical device via an applicator, which can be a spray applicator through a trocar, catheter, endoscope or other minimally invasive device, onto a specific location(s) that a surgeon or other practitioner has identified as particularly susceptible to or concerning for development of fibrous adhesions. In another aspect, the administering can be done after opening of the surgical wound but before the surgical procedure; during the surgical procedure, or after the surgical procedure but before the surgical wound has been closed. If desired, the liquid medical composition or medical device can also be administered after the surgery is completed (for example through a syringe and needle) and can be administered to non-surgical target sites as well. The surgical site of the patient can be, for example, at least one of the pelvic cavity, abdominal cavity, dorsal cavity, cranial cavity, spinal cavity, ventral cavity, thoracic cavity, pleural cavity, pericardial cavity, skin, joints, muscles, tendons or ligaments. The administering of the fucan-low endotoxin medical composition or medical device into the surgical site of the patient can be accomplished in less than about 15 minutes, 10 minutes, 8 minutes, 6 minutes, 5 minutes, 4 minutes, 3 minutes, 2 minutes, 1 minute, 45 seconds, 30 seconds, 20 seconds, 15 seconds, 10 seconds and 5 seconds.

Examples of administering the fucan-low endotoxin medical composition or medical device to a surgical site include without limitation administering the fucan-low endotoxin medical composition or medical device at the surgical site of a Cesarean section surgical procedure; a microvascular free flap reconstruction surgical procedure, a full thickness skin graft surgical procedure, a V-Y advancement flap surgical procedure, a fasciocutaneous rotation flap surgical procedure, an arthroplasty surgical procedure, a mastectomy surgical procedure, a sequestrectomy surgical procedure, a saucerization surgical procedure, an osteotomy surgical procedure, an osteoplasty surgical procedure, a patellectomy surgical procedure, a synovectomy surgical procedure, a capsulectomy surgical procedure, a tendon or ligament repair surgical procedure, a tenolysis surgical procedure, a tenotomy surgical, a fasciotomy surgical procedure, a meniscal repair surgical procedure, a vertebrectomy surgical procedure, a ethmoidectomy surgical procedure, a Caldwell Luc's operation surgical procedure, a dacryocystorhinostomy surgical procedure, a lysis nasal synechia surgical procedure, a thymectomy surgical procedure, a pneumonolysis surgical procedure, a pneumonectomy surgical procedure, thoracoplasty surgical procedure, a bilobectomy surgical procedure, a portal hypertension surgery surgical procedure, a splenectomy surgical procedure, a esophagectomy surgical procedure, a peritonitis surgery surgical procedure, a gastrectomy surgery surgical procedure, a jejunojejunostomy surgery surgical procedure, a laparoscopic cholecystectomy surgery surgical procedure, a laparoscopic common bile duct exploration surgical procedure, a gastroenterostomy surgical procedure, a bariatric surgery surgical procedure, a bowel resection & anastomosis surgical procedure, a segemental hepatectomy surgical procedure, a lobectomy surgical procedure, a pancreatomy surgical procedure, a pancreaticoduodenectomy surgical procedure, a tumor resection surgical procedure, a laparoscopic nephrectomy surgical procedure, a cystectomy surgical procedure, an abdominal or pelvic adhesion lysis surgical procedure, a hysterosalpingostomy surgical procedure, a salpingoplasty surgical procedure, an ectopic pregnancy laparoscopic surgery surgical procedure, a joint replacement surgery surgical procedure, a broken bone repair surgical procedure, a hysterectomy surgical procedure, a gallbladder removal surgical procedure, a heart bypass surgical procedure, an angioplasty surgical procedure, an atherectomy surgical procedure, a breast biopsy surgical procedure, a carotid endarterectomy surgical procedure, a cataract surgery surgical procedure, a coronary artery bypass surgical procedure, a dilation and curettage surgical procedure, a hernia repair surgical procedure, a lower back pain surgery surgical procedure, a partial colectomy surgical procedure, prostatectomy surgical procedure and a tonsillectomy surgical procedure, after opening the surgical wound, during surgery, before closing the surgical wound and/or after closing the surgical wound.

Cancers Generally

Cancer has been the second leading cause of death in the U.S. and accounts for over 20% of all mortalities. Cancer is a proliferative disease and is characterized by the uncontrolled division of certain cells, which may lead to the formation of one or more tumors. A number of methods are used to treat cancer, including surgery, radiation, chemotherapy and combinations thereof. Although surgery is a relatively common method used for some localized tumors, there is still a significant chance of tumor recurrence after tumor excision.

Treating cancers and other proliferative diseases has been limited by the potential for damage or toxicity to non-cancerous, healthy tissues. In radiation and surgical treatments, the procedure has been generally confined to and proximal to the tumor sites. However, there can be significant risk to patients undergoing surgical removal of cancerous tissues (e.g., in removal of prostate or brain tumors there can be a significant risk of non-repairable damage to surrounding vital tissues, for example via potential reduced need for resection of non-tumor tissues. Furthermore, in focused radiation treatment, which has been given as a first line treatment for prostate cancer, there are similar risks. In the chemotherapeutic treatment of cancer, the drug has been administered systemically, so that the whole body is exposed to the drug. These drugs are designed to be toxic to cancer cells, but they are also (generally) toxic to non-cancerous cells so that patients become quite ill when undergoing drug treatments for cancer. Through experience, oncologists are able to give doses of these drugs that may be tolerated by some patients. However, these doses are often not successful in treating cancers.

One problem with any method of treating cancer has been the local recurrence of the disease. For example, approximately 700,000 Americans are diagnosed with localized cancer annually (approximately 64% of all cancer patients) and almost half a million are treated using surgical methods. Unfortunately, 32% of patients treated with surgery relapse after the initial treatment (approximately 21% relapse at the initial surgical site and 11% at distant metastatic sites). Almost 100,000 patients die annually due to localized recurrence of cancer. This has been especially true in breast cancer where 39% of patients undergoing lumpectomy will experience local recurrence of the disease.

Staging is a method of judging the progress of the cancer (solid tumor) in a patient. A simplified approach puts patients into three groups or stages based on how far the cancer has advanced:

Stage 1: The cancer can be treated by surgically removing part of the organ. This is also known as the resectable stage.

Stage 2: The cancer has advanced past the point of being resectable but is still confined to the organ itself.

Stage 3: The tumor has spread to other organs.

Many cancers are treated with anti-proliferative agents including, for example, 5-fluorouracil (Efudex-), vinca alkaloids (for example, vincristine (Oncovin-)), anthracyclines (for example, doxorubicin (Adriamycin¯)), cisplatin (Platinol-AQ¯), gemcitabine hydrochloride (Gemzar-), methotrexate and paclitaxel. Some examples of the toxicities associated with the anti-proliferative agents, methotrexate and paclitaxel, are discussed elsewhere herein. Methotrexate has been used to treat several cancers including, for example, bladder, breast, cervical, head and neck, hepatic, lung, and testicular cancers. Paclitaxel has been used to treat several cancers including, for example, ovarian, breast, and non-small cell lung cancers (*Compendium of Pharmaceutical and Specialties Thirty-fifth Edition,* 2000).

Toxicities due to 5-fluorouracil can include cardiovascular toxicity such as myocardial ischemia; central nervous system toxicities such as euphoria, acute cerebellar syndrome and ataxia; dermatologic toxicities such as alopecia and dermatitis; gastrointestinal toxicities such as nausea, vomiting and oral or gastrointestinal ulceration; hematologic toxicities such as leukopenia, thrombocytopenia and anemia; hypersensitivity toxicities such as anaphylaxis and contact hypersensitivity; ocular toxicities such as increased lacrimation, photophobia and conjunctivitis; and, other toxicities such as fever. 5-fluorouracil has been used to treat many cancers including, for example, breast, colorectal, gastric, hepatic, bladder, head and neck, non-small cell lung, ovarian, pancreatic, and prostate cancers (*Compendium of Pharmaceutical and Specialties Thirty-fifth Edition,* 2000).

Toxicities due to vincristine include central nervous system toxicities such as seizures in children and hallucinations; dermatologic toxicity such as alopecia; extravasation toxicity such as vesicant; gastrointestinal toxicities such as nausea, vomiting, constipation and stomatitis; hematologic toxicity such as myelosuppression; neurologic toxicities such as peripheral neuropathy and autonomic neuropathy; ocular toxicities such as double vision, transient blindness and optic atrophy; renal/metabolic toxicities such as urinary retention, hyperuricemia and bladder atony; respiratory toxicity such as shortness of breath; and, other toxicity such as fever in children. This anti-proliferative agent has been used to treat several cancers including, for example, Hodgkin's disease, small cell lung, Wilm's tumor, and testicular cancers (*Compendium of Pharmaceutical and Specialties Thirty-fifth Edition,* 2000).

Toxicities due to doxorubicin include cardiovascular toxicities such as electrocardiographic abnormalities and cardiomyopathy; dermatologic toxicities such as alopecia and nail changes; extravasation hazard toxicity such as vesicant; gastrointestinal toxicities such and nausea, vomiting and stomatitis; genitourinary toxicity such as red coloration of urine; hematologic toxicity such as myelosuppression; hypersensitivity toxicities such as anaphylaxis and skin rash; ocular toxicity such as conjunctivitis; reproductive toxicity such as infertility; and, other toxicity such as hyperuricemia. This anti-proliferative agent has been used to treat several cancers including, for example, breast, small cell lung, and ovarian cancers (*Compendium of Pharmaceutical and Specialties Thirty-fifth Edition,* 2000).

Toxicities due to cisplatin include cardiovascular toxicity such as electrocardiographic changes; dermatologic toxicity such as hyperpigmentation; extravasation hazard toxicity such as irritant; gastrointestinal toxicities such as nausea and vomiting; hematologic toxicities such as myelosuppression and hemolytic anemia; hypersensitivity toxicity such as anaphylactic; neuromuscular toxicity such as peripheral neuropathy and acute encephalopathy; ocular toxicity such as retrobulbar neuritis; otologic toxicities such as hearing loss and tinnitus; renal/metabolic toxicities such as toxic nephropathy and hypokalemia; and, other toxicity such as infertility. This anti-proliferative agent has been used to treat several cancers including, for example, bladder, small cell lung, ovarian, testicular, brain, breast, cervical, head and neck, hepatoblastoma, and thyroid cancers (*Compendium of Pharmaceutical and Specialties Thirty-fifth Edition,* 2000). Toxicities due to gemcitabine hydrochloride include, for example, hematologic toxicities such as myelosuppression; gastrointestinal toxicities such as nausea, vomiting and stomatitis; hepatic toxicities such as transient elevations of serum transaminases; renal toxicities such as proteinuria, hematuria, hemolytic uremic syndrome and renal failure; dermatologic toxicity such as rash and alopecia; edema toxicities such as edema and peripheral edema; and, other toxicity such as fever. This anti-proliferative agent has been used to treat pancreatic and non-small cell lung cancers (*Compendium of Pharmaceutical and Specialties Thirty-fifth Edition,* 2000).

The present discussion comprises prevention or treatment of localized cancers or solid tumors that can be treated include those of the prostate, breast, pancreas, liver, kidney, genitourinary system, brain, gastrointestinal system, respiratory system, and head and neck. The compositions, etc., herein may prevent or treat cancers, including metastases, by allowing controlled release of a fucan-low endotoxin composition at a site somewhat distant from the target tumors by allowing effective concentrations of the fucan-low endotoxin composition to reach the tumors and/or metastases by diffusion or even systemic transport. Some of these cancers are discussed further in the following paragraphs.

Prostate Cancer

Prostate cancer is a malignant tumor that arises in the cells lining the prostate gland. In the U.S., an estimated 200,000 patients will develop prostate cancer this year, and more than 30,000 will die of the disease. Prostate cancer has a death to new cases ratio of ~15%. The cancer may remain within the prostate, or it may spread to surrounding tissues or to distant sites (most often lymph nodes and bone). Usually prostate cancer spreads silently, producing symptoms only when it has progressed beyond the prostate. If prostate cancer has been diagnosed and treated during early stages, in some studies patients have had a 5-year survival rate of 94%.

Prostate cancer is often discussed as a disease of men over age 50. In fact, 80% of men with prostate cancer are 60 years of age and older. A man's chances of being diagnosed with prostate cancer during his lifetime are about 1 in 10, roughly the same as a woman's chances of having breast cancer. The number of reported new cases has risen dramatically in recent years as a result of improved tests that can detect the disease early in its development, often long before symptoms appear. The likelihood of developing prostate cancer in any given year increases with age but rises dramatically after age 50.

Current treatment options for prostate cancer depend upon the extent of disease progression, the patient's age and overall health. Elderly patients, who have only early stage cancer or who suffer from additional, more serious diseases, may be treated conservatively, whereas those whose cancer is advanced may undergo more aggressive treatment. Prostate cancer has been treated by various methods, including radiation therapy (external beam radiation or brachytherapy), hormone withdrawal or castration (surgical or chemical), anti-proliferative agents, surgery, and expectant therapy (that is, "watchful waiting"). No treatment guarantees an absolute cure, and some have considerable side effects.

Early stage prostate cancer (that is, the tumor is localized to the prostate) may be treated with "watchful waiting". Surgery for prostate cancer has been recommended for patients whose overall health has been otherwise good and the tumor is confined to the prostate gland. A common treatment for localized cancer of the prostate in men under the age of 70 has been radical prostatectomy (that is, surgical removal of the prostate).

Patients whose cancer is localized in the prostate area are commonly treated with external beam radiation (EBR). The radiation kills cancer cells and shrinks tumors. EBR accounts for less than 20% of localized prostate cancer treatment, with approximately 50% of these patients experiencing post radiation recurrences of the disease. Combined with early stage prostate cancer detection and increased demand from patients, brachytherapy (i.e., local radiation therapy) use has been expected to grow. In 1995, only 2.5% of newly diagnosed patients were treated using brachytherapy. Brachytherapy involves the implantation of radioactive metal "seeds" in the prostate tumor.

Treatment for prostate cancer that has spread involves removal of the testicles or hormone therapy. Both are used to inhibit or stop the production of the testosterone that has been driving the cancer growth. Approximately 20% of all prostate cancer patients undergo hormone withdrawal therapy. Hormone therapies include goserelin acetate (Zoladex$^{-}$) or leuprolide acetate (Lupron$^{-}$). Anti-proliferative agents used to treat prostate cancer have included 5-fluorouracil.

Breast Cancer

In the U.S., breast cancer has been the most common cancer among women, with about 180,000 new cases diagnosed every year (male breast cancer accounts for about 5% of all diagnosed breast cancers). It has been surpassed only by lung cancer as a cause of death in women, and it has been responsible for approximately 50,000 deaths annually. An American woman has a one in eight (or about 13%) chance of developing breast cancer during her lifetime. Over the past decade, most reported breast cancers were small, primary (arising independently; not caused by a metastasis) tumors. Roughly 70% to 80% of newly diagnosed patients exhibited early-stage disease (Stage 1 or 2), and a majority had no involvement of the axillary (underarm) lymph nodes.

Most breast cancers are carcinomas (that is, malignant tumors that grow out of epithelial tissues). Less than 1% of breast cancers are sarcomas, or tumors arising from connective tissue, bone, muscle or fat. In addition, most breast cancers (about 75%) are ductal carcinomas, arising in the tissues that line the milk ducts. A much smaller number of cancers (about 7%) are found within the breast lobules and are called lobular carcinomas. Paget's disease (cancer of the areola and nipple) and inflammatory carcinoma account for nearly all other forms of breast cancer.

Breast cancer treatment has been complicated and depends on many factors. Two important factors are the type of tumor and the stage of progression. Tumor characteristics, in particular, help to separate individuals into two groups: (1) those who are at low risk of cancer recurrence and (2) those who are at high risk of cancer recurrence. Specific prognostic factors place patients in either of these groups. These factors include tumor size; presence of female sex hormone estrogen and progesterone (ER/PR) receptors; cellular growth cycle phase (whether tumor cells are actively dividing or are in "S-phase"); presence of a protein known as "her-2-neu protein"; tumor grade, an indicator of tumor cell differentiation or change; and, tumor ploidy, the number of sets of genetic material within tumor cells.

Treatment of primary disease without significant lymph node involvement has been by lumpectomy and radiotherapy. More significant lymph node involvement may warrant mastectomy and removal of auxiliary lymph nodes. At this stage the chance of metastasis and local recurrence has been high. Treatment of metastatic disease has been palliative, involving radiation therapy and chemotherapy, which are immunosuppressive, cytotoxic and leukopenia. Anti-proliferative agents including, for example, 5-fluorouracil, doxorubicin, methotrexate, and paclitaxel, have been approved for use against breast cancer.

Pancreatic Cancer

The pancreas is an organ of the digestive system located near the stomach and small intestine. It has two major functions: the production of enzymes and hormones. Cancers of the pancreas can occur in the exocrine (i.e., enzymes) pancreas (e.g., classic pancreatic adenocarcinomas) or can occur in the endocrine (i.e., hormones) pancreas.

Cancers of the exocrine pancreas are a very serious health issue. In the U.S., approximately 28,000 patients are diagnosed with pancreatic cancer, while about the same number die annually from this disease. Pancreatic cancer occurs equally in males and females. Due to difficulties in diagnosis, the intrinsic aggressive nature of pancreatic cancers, and the sparse systemic treatment options available, only approximately 4% of patients diagnosed with pancreatic adenocarcinoma live for 5 years after diagnosis. Pancreatic cancer has been the $5^{th}$ leading cause of cancer death, following breast, lung, colon, and prostate cancer.

The choice of treatment for pancreatic cancer depends largely on the stage of the tumor. Possible treatments include surgery, anti-proliferative agents, radiation, and biological therapy. Surgery has been usually reserved for Stage 1 patients whose cancer is deemed resectable. Sometimes a combination of therapies, such as radiation and anti-proliferative agent given before or after surgery, can increase a patient's chances of survival. Pancreatic cancer that is deemed unresectable (usually Stage II or later) may be treated using anti-proliferative agents in clinical trials. Anti-proliferative agents, such as, for example, gemcitabine or 5-fluorouracil have had some effect against pancreatic cancer and gemcitabine has been used as a palliative agent. Toxicities due to these anti-proliferative agents are discussed elsewhere herein. Radiation therapy has some effect against pancreatic cancer when used in combination with chemotherapy. Radiation therapy alone may subdue symptoms. This form of treatment has also been used in Stage II or later pancreatic cancers.

Bladder Cancer

In 1998, it was estimated that over 54,000 new cases of bladder cancer would be diagnosed in the U.S. and about 15,000 deaths would be attributed to the disease. Bladder cancer has been the fourth most common cancer among American men and the ninth most common cancer among American women. It occurs three times more frequently in men than in women. Primarily a disease of older men, bladder cancer has been a significant cause of illness and death. The risk of bladder cancer increases steeply with age (80% of cases occur in people older than 50 years), with over half of all bladder cancer deaths occurring after age 70. In white men over 65, the annual disease rate of bladder cancer has been approximately 2 cases per 1,000 persons; this contrasts with a rate of 0.1 cases per 1,000 persons under 65. During one's lifetime, the probability of developing bladder cancer has been greater than 3%; however, the probability of dying, from bladder cancer has been small (<1%). Bladder cancer rarely occurs in people who are younger than 40 years of age.

Recent studies suggest that certain genes and inherited metabolic abilities may play a role in bladder cancer. Transitional cell carcinoma (TCC) has been the most common form of bladder cancer. TCC usually occurs as a superficial (surface), papillary (wart-like), exophytic (outward-growing) mass upon a stalk-like base. In some cases, though, TCC may be attached on a broad base or it may appear ulcerated (within an indented lesion). Papillary TCCs often start out as areas of hyperplasia that later dedifferentiate or lose individual cell characteristics. Only about 10% to 30% of papillary TCCs develop into invasive cancers. By contrast, nonpapillary forms of TCC are more likely to become invasive. As noted, such TCCs may appear ulcerated or flat. Flat, nonpapillary TCC that has been made up of anaplastic epithelium has been classified as carcinoma in situ (CIS or TIS). The tissue of CIS contains cells that are large, have noticeable nucleoli (round body within a cell; involved in protein synthesis), and lack normal polarity.

The treatment of bladder cancer depends upon many factors. The most important of these factors are the type of tumor that is present and its stage. Common treatments include transurethral resection (TUR), electrosurgery, laser surgery, intravesical therapy, anti-proliferative agents, surgical therapy, cystectomy, and radiation therapy. Examples of anti-proliferative agents used to treat bladder cancer include, for example, 5-fluorouracil, cisplatin and methotrexate. Toxicities due to the anti-proliferative agents, 5-fluorouracil, cisplatin, and methotrexate, are discussed elsewhere herein.

Brain Cancer

Brain tumors are often inoperable and more than 80% of patients die within 12 months of diagnosis. Approximately 18,000 new cases of primary intracranial (brain) cancer are diagnosed each year in the U.S. This represents about 2 percent of all adult cancers. More than 50 percent of these are high-grade gliomas (i.e., glioblastoma multiform and anaplastic astrocytoma tumors). Patients with these tumors often suffer from severe disabilities such as motor dysfunction, seizures, and vision abnormalities.

Tumors that begin in brain tissue are known as primary brain tumors. Primary brain tumors are classified by the type of tissue in which they begin. The most common brain tumors are gliomas, which begin in the glial (supportive) tissue. Others include astrocytomas, brain stem gliomas, ependymomas and oligodendrogliomas.

Surgical removal of brain tumors has been recommended for most types and in most locations and should be as complete as possible within the constraints of preservation of neurologic function. An exception to this rule has been for deep-seated tumors, such as pontine gliomas, which are diagnosed on clinical evidence and are treated without initial surgery approximately 50% of the time. In many cases, however, diagnosis by biopsy is performed. Stereotaxic biopsy can be used for lesions that are difficult to reach and resect. Patients who have brain tumors that are either infrequently curable or unresectable should be considered candidates for clinical trials that evaluate radiosensitizers, hyperthermia, or interstitial brachytherapy used in conjunction with external-beam radiation therapy to improve local control of the tumor or for studies that evaluate new drugs and biological response modifiers.

Radiation therapy has a major role in the treatment of most tumor types and can increase the cure rate or prolong disease-free survival. Radiation therapy may also be useful in the treatment of recurrences in patients treated initially with surgery alone. Chemotherapy may be used before, during, or after surgery and radiation therapy. Recurrent tumors are treated with chemotherapy as well. Anti-proliferative agents used in the treatment of brain cancers include cisplatin. Examples of the toxicities associated with this anti-proliferative agent are discussed elsewhere herein.

Restenosis

Restenosis is a form of chronic vascular injury leading to vessel wall thickening and loss of blood flow to the tissue supplied by the blood vessel. This inflammatory disease can occur in response to vascular reconstructive procedures including any manipulation that relieves vessel obstruction. Thus, restenosis has been a major restrictive factor limiting the effectiveness of these procedures.

The present discussion comprises prevention or treatment of restenosis, for example by administering to a blood vessel a therapeutically effective amount of the combination of an oligonucleotide therapeutic and an anti-inflammatory agent. Suitable compositions include a polymeric carrier that can be surgically implanted at a restenosis site, or potential restenosis site, or can be injected via a catheter as a polymeric paste or gel. Suitable compositions may comprise fucan-low endotoxin compositions discussed herein.

Arthritis

Rheumatoid arthritis (RA) is a debilitating chronic inflammatory disease characterized by pain, swelling, synovial cell proliferation (pannus formation) and destruction of joint tissue. In the advanced stage, the disease often damages critical organs and may be fatal. The disease involves multiple members of the immune system (macrophages/monocytes, neutrophils, B cells and T cells) complex cytokine interactions and synovial cell malfunction and proliferation. Early aggressive treatment has been recommended with disease modifying anti-rheumatic drugs (DMARDs) such as methotrexate, which drug is discussed elsewhere herein.

Crystal induced arthritis has been characterized by crystal induced activation of macrophages and neutrophils in the joints and is followed by excruciating pain for many days. The disease progresses so that the intervals between episodes gets shorter and morbidity for the patient increases. This disease has been generally treated symptomatically with non-steroidal anti-inflammatory drugs (NSAIDs) such as diclofenac sodium (Voltaren□). This anti-inflammatory agent has toxicities which include central nervous system toxicities such as dizziness and headache; dermatologic toxicities such as rash and pruritus; gastrointestinal toxicities such as exacerbated ulcerative colitis and Crohn's disease; genitourinary toxicities such as acute renal failure and renal papillary necrosis; hematologic toxicities such as agranulocytosis, leukopenia and thrombocytopenia; hepatic toxicities such as elevated liver transaminases and hepatitis; and, other toxicities such as asthma and anaphylaxis.

The present discussion comprises prevention or treatment of rheumatoid arthritis, for example via administering to a patient a therapeutically effective amount of an oligonucleotide therapeutic and optionally an anti-inflammatory agent. Suitable compositions include a polymeric carrier that can be injected into a joint as a controlled release carrier of the anti-inflammatory agent and microparticulates as controlled release carriers of the oligonucleotide therapeutic (which in turn has been incorporated in the polymeric carrier). Suitable compositions may comprise fucan-low endotoxin compositions discussed herein. Such polymeric carriers may take the form of polymeric microspheres, pastes or gels.

Inflammatory Conditions

The compositions, etc., herein may optionally inhibit or treat inflammatory conditions involving neutrophils for example comprising administering to a patient compositions containing an oligonucleotide therapeutic and an anti-inflammatory agent. Examples of such conditions include crystal-induced arthritis; osteoarthritis; non-rheumatoid inflammatory arthritis; mixed connective tissue disease; Sjögren's syndrome; ankylosing spondylitis; Behçet's syndrome; sarcoidosis; psoriasis; eczema; inflammatory bowel disease; chronic inflammatory lung disease; neurological disorders; and, multiple sclerosis. Some of these diseases are discussed further in the following paragraphs.

Chronic Inflammatory Skin Diseases (Including Psoriasis and Eczema)

Psoriasis is a common, chronic inflammatory skin disease characterized by raised, thickened and scaly lesions which itch, burn, sting and bleed easily. While these diseases have cellular proliferation and angiogenic components in later stages of the disease, patients often have accompanying arthritic conditions. Symptoms may be treated with steroidal anti-inflammatory agents such as prednisone or anti-proliferative agents such as methotrexate, which agents are discussed elsewhere herein. The compositions herein may also be used to inhibit or otherwise treat and/or prevent chronic inflammatory skin diseases, for example psoriasis and/or eczema.

The following provides some additional representative examples of inflammatory diseases that can be treated with compositions discussed herein, include, for example, arterial embolization in arteriovenous malformations (vascular malformations); menorrhagia; acute bleeding; central nervous system disorders; and, hypersplenism; inflammatory skin diseases such as psoriasis; eczematous disease (atopic dermatitis, contact dermatitis, eczema); immunobullous disease; and, inflammatory arthritis which includes a variety of conditions including rheumatoid arthritis, mixed connective tissue disease, Sjögren's syndrome, ankylosing spondylitis, Behçet's syndrome, sarcoidosis, crystal induced arthritis and osteoarthritis (all of which feature inflamed, painful joints as a prominent symptom).

Ischemia

Ischemia or ischaemia involves a restriction in blood supply, which may include a shortage of supply of oxygen, glucose and other components required for proper tissue function, resulting in damage and/or dysfunction of tissue. Ischemia can cause severe problems. For example, tissues can become anoxic, necrotic, and clots can form. Various attempts have been made to prevent and/or treat ischemia. For example, restoration of blood flow, or reperfusion. Restoration of blood, however, involves the reintroduction of oxygen, which can cause additional damage due to the production of free radicals, resulting in reperfusion injury. Reperfusion injury can cause severe problems. The compositions herein may be used to inhibit or otherwise treat and/or prevent, ischemia, and/or reperfusion injury.

Endotoxemia

Endotoxemia is the presence of endotoxins in the blood. Endotoxemia can cause severe problems. For example, endotoxemia can lead to septic shock. The compositions herein may be used to inhibit, or otherwise treat and/or prevent, endotoxemia.

Keloid Scarring

Keloid trait causes wounds to heal with raised scars. Keloid traits' raised scars involve abnormal fibrous scarring. Keloid trait causes severe problems, for example, pain and disfigurement. The compositions herein may be used to inhibit, or otherwise treat and/or prevent, keloid trait and its resulting raised scars.

Keloid (keloid scar) is a type of scar that expands in growths over normal skin. Keloids involve abnormal collagen growth, including type I and type III collage abnormal growth. Keloids cause severe problems, for example, pain, itchiness, and if infected may ulcerate. Attempts have been made to treat or prevent keloids including the use of surgery, dressings, steroid injections and laser therapy. The compositions herein may be used to inhibit, or otherwise treat and/or prevent, keloids.

Dermatitis

Dermatitis includes inflammation of the skin including atopic dermatitis and contact dermatitis. For example, contact dermatitis involves localized rash and/or irritation of the skin following contact of the skin with a foreign substance. For example, atopic dermatitis is a chronically relapsing, pruritic skin disease. Atopic dermatitis is sometimes called prurigo Besnier, neurodermitis, endogenous eczema, flexural eczema, infantile eczema, childhood eczema and prurigo diathsique. Eczema is a disease in a form of dermatitis. Other types of dermatitis include spongiotic dermatitis, seborrhoeic dermatitis (dandruff), dyshidrotic dermatitis (pompholyx), urticaria, vesicular dermatitis (bullous dermatitis), and popular urticaria. Dermatitis can cause severe problems. For example, dry skin, skin rashes, skin edema, skin redness, skin itchiness, skin crusting, cracking, blistering, oozing and bleeding. Attempts have been made to treat or prevent dermatitis including the use of corticosteroids and coal tars. The compositions herein may be used to inhibit, or otherwise treat and/or prevent, dermatitis including atopic dermatitis, eczema, contact dermatitis, spongiotic dermatitis, seborrhoeic dermatitis, dyshidrotic dermatitis, urticaria, vesicular dermatitis, and popular urticaria.

Rosacea

Rosacea is a chronic disease or condition typically characterized by facial erythema. Rosacea can cause severe problems. For example, rosacea typically begins as redness on the forehead, nose or cheeks and can also cause redness on the neck, ears, scalp and chest. For example, rosacea can cause additional symptoms including telangiectasia, papules, pustules, painful sensations, and in advanced cases rhinophyma (red lobulated nose) may develop. Rosacea subtypes include erythematotelangiectatic rosacea, papulopustular rosacea, phymatous rosacea, and ocular rosacea. Attempts have been made to treat or prevent rosacea including the use of anti-inflammatories and antibiotics. The compositions herein may be used to inhibit, or otherwise treat and/or prevent, rosacea including its erythematotelangiectatic, papulopustular, rosacea and ocular subtypes.

Medical Device, Medical Material, Combination, and Pharmaceutical Products

The discussion herein also provides medical devices, medical materials, combination, and pharmaceutical products, comprising compositions as discussed herein in a medical device, medical materials, combination product or pharmaceutically acceptable container. The products can also include a notice associated with the container, typically in a form prescribed by a governing agency regulating the manufacture, use, or sale of medical devices, medical materials, combination, and pharmaceuticals or biopharmaceuticals, whereby the notice is reflective of approval by the agency of the compositions, such as a notice that a fucan-low endotoxin composition has been approved as an anti-proliferative agent or anti-inflammatory agent, e.g., for human or veterinary administration to treat proliferative diseases or inflammatory diseases (such as, for example, inflammatory arthritis, restenosis, surgical adhesions, psoriasis and peritonitis). Instructions for the use of the fucan-low endotoxin composition herein may also be included. Such instructions may include information relating to the dosing of a patient and the mode of administration. The products can also include devices, systems, etc., to administer or apply the medical materials, such as, for example, a syringe and/or a spray applicator.

The present application is further directed to methods of making the various elements of the fucan-low endotoxin compositions, systems etc., discussed herein, including making the compositions themselves, as well as to methods of using the same, including for example treatment of the conditions, diseases, etc., herein.

The present application further comprises medical devices, medical materials, medical combination products, and pharmaceutical products for treatment of fibrous adhesions, arthritis, psoriasis or other diseases as desired comprising fucan-low endotoxin compositions presented herein. The materials, etc., can be used in a medicament for treating fibrous adhesions, such as a surgical adhesions, arthritis, psoriasis or other diseases as desired. Also provided are methods of manufacturing and using such medicaments able to reduce symptoms associated with at least one of fibrous adhesions, arthritis, and psoriasis in a patient including a human patient, comprising combining a pharmaceutically effective amount of a fucan such as fucoidan as discussed herein with a pharmaceutically acceptable excipient or buffer.

The following Examples provide exemplary discussions of certain embodiments herein but the disclosure and claims are not limited thereto.

Example 1: Chemical Structural Modification

An exudate-extract was obtained from *Laminaria hyperborea*. The exudate-extract was filtered and small molecules were removed by tangential flow filtration (TFF) over a 100 kDa filter. A sample of the resulting retentate was lyophilized to obtain otherwise unmodified sample A. The resulting retentate was brought to 0.25 M NaOH by addition of 10 M NaOH solution and left at room temperature for 16 hours. The resulting sample was then centrifugally filtered over a 50 kDa filter and the resulting retentate collected and lyophilized to obtain base-treated sample B. Both of unmodified sample A and base-treated sample B were analyzed by proton nuclear magnetic resonance spectroscopy ($^{1}$H-NMR) and the resulting $^{1}$H-NMR spectrum are shown in FIG. 3A.

Figure 3A:
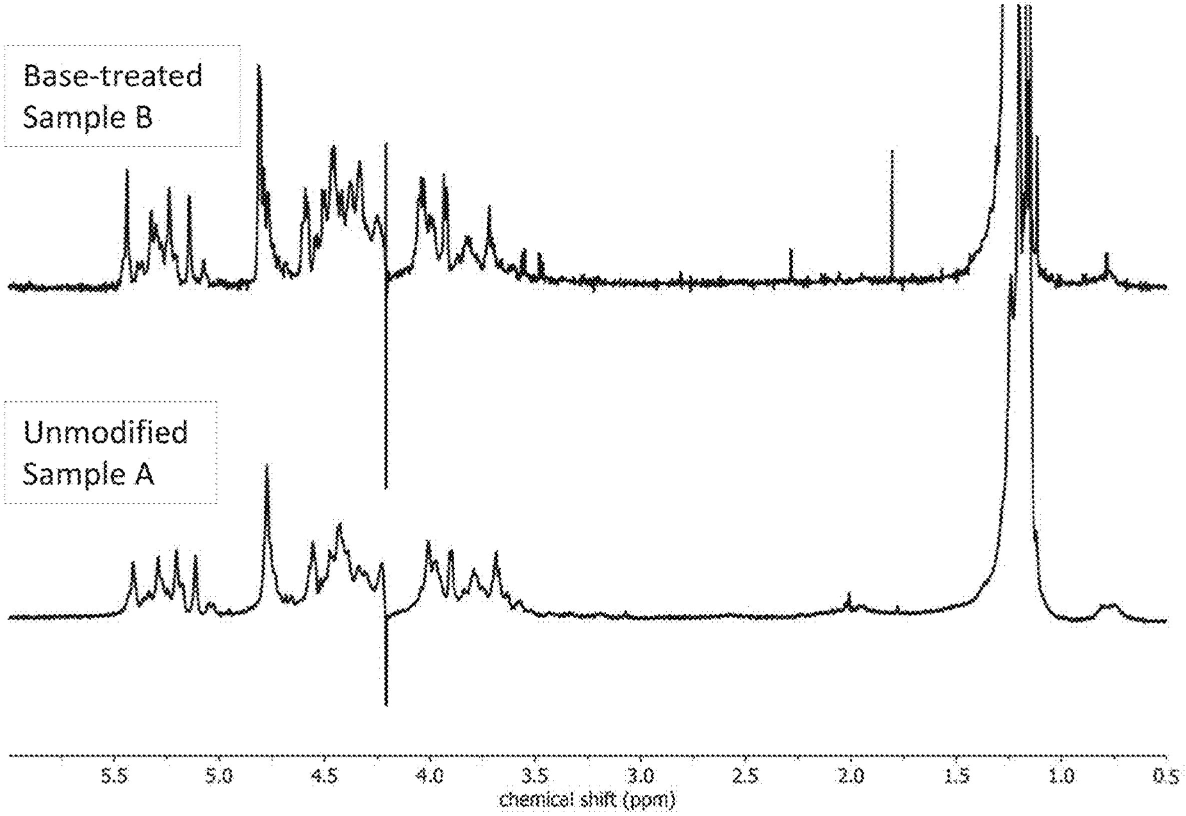
FIG. 3A depicts NMR results demonstrating that certain fucans treated according to methods herein undergo chemical structural changes to the fucans.

FIG. 3A demonstrates the chemical structural modification of the fucan accomplished, the broad peak with a chemical shift about 2.0 ppm that is present in the unmodified sample A is not present in the base-treated sample B.

Unmodified sample A and base-treated/modified sample B were further analyzed by 2D $^{1}$H-$^{13}$C heteronuclear multiple quantum coherence (HMQC). The HMQC spectra, shown in FIG. 3B, were acquired at 70° C. with solvent signal suppression on a 600 MHz spectrometer equipped with 5-mm cold probe. A high number of scans of the HMQC spectra were acquired in the range from 10-30 ppm in the carbon dimension in 8 increments of 256-512 scans each; such scans were combined to create the spectra in FIG. 3B.

Figure 3B:
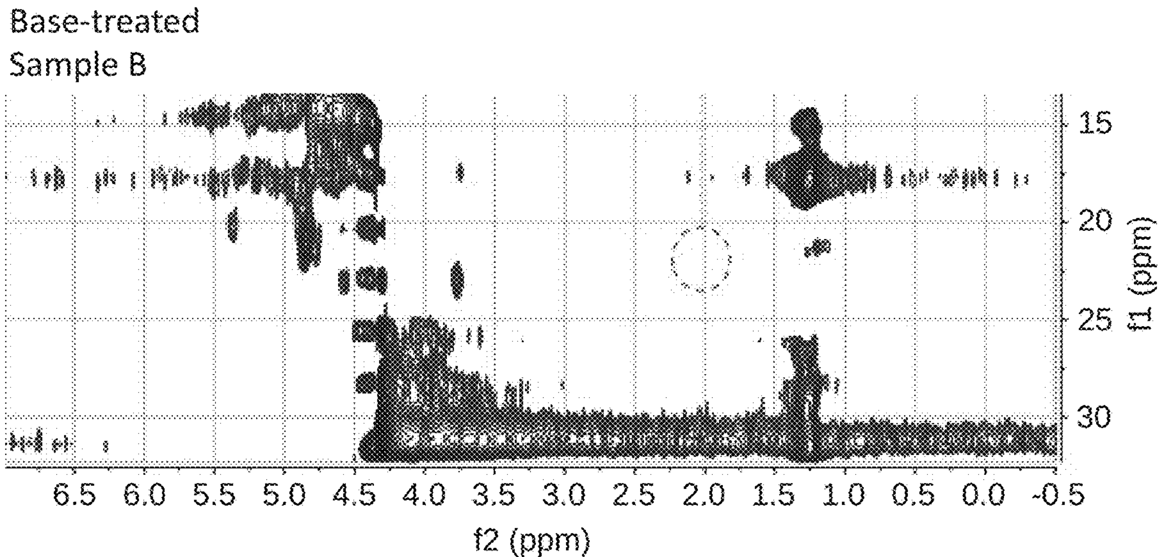
FIG. 3B depicts 2-D NMR results demonstrating that certain fucans treated according to methods herein undergo chemical structural changes to the fucans.
Figure 3B:
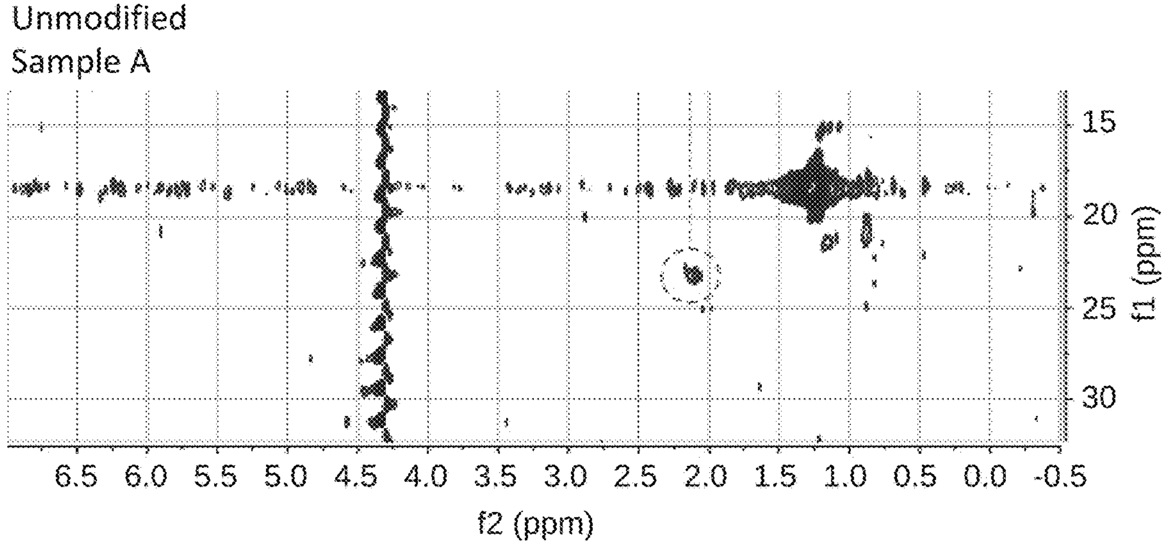

The HMQC spectra for unmodified sample A has a cross-peak corresponding to O-acetyl groups, indicated by the signal circled in FIG. 3B. This cross-peak is not present in the spectra for base-treated sample B. This demonstrates the removal of acetyl groups from the fucan, and thus chemical structural modification of the fucan in base-treated sample B by the NaOH treatment.

Example 2: Physically Induced Flocculation

A feedstock fucoidan composition containing a high level of endotoxin, for example at least 1000 endotoxin units per milligram of fucoidan (EU/mg) is prepared at about 10% w/v in distilled water to obtain a starting solution. Sodium chloride is added to the starting solution, to produce a mixture with a final sodium chloride concentration of about 0.1 M. The mixture is heated to near boiling for between 10-15 minutes. Treatment of the mixture at this temperature induces flocculation of dissolved impurities and particulate non-fucoidan matter. The mixture is centrifuged at 2300 gravities for 40 minutes to separate the fucoidan containing solution from the flocculated non-fucoidan components. The fucoidan containing solution is lyophilized to obtain a fucoidan-low endotoxin composition containing a significantly reduced level of endotoxin units per milligram of fucoidan (EU/mg), for example about 100 EU/mg. The EU levels can be measured, for example, by turbidimetric limulus amebocyte lysate (LAL) assay.

Example 3: Modified Tangential Flow Filtration

A crude fucoidan composition was first subjected to the physically induced flocculation method discussed in Example 2 to provide a starting fucoidan composition containing 109 EU/mg as determined by turbidimetric limulus amebocyte lysate (LAL) assay. This 109 EU/mg composition was then dissolved at 50 mg/ml in deionized water and filtered through a 0.22 μm filter to obtain a starting solution. The starting solution was diafiltered for 2 diavolumes with a solution of 0.01 M ethylenediamine-tetraacetic acid (EDTA) and 0.5% w/v sodium deoxycholate to digest and remove biological contaminants and biological lysate components such as endotoxin. The resulting first retentate fucoidan composition was diafiltered for 10 diavolumes with 0.01 M EDTA for the removal of residual sodium deoxycholate, and then with 5 diavolumes of distilled water to a final pH of 7. The resulting second retentate fucoidan composition was analyzed for endotoxin by the turbidimetric LAL method and lyophilized to determine the fucoidan content. The endotoxin level of the fucoidan-low endotoxin composition in solution was found to be 0.158 EU/mg.

Example 4. Tangential Flow Filtration

A starting fucoidan composition dissolved in deionized water was microfiltered through three different filters having progressively smaller pore size, with the last filter being a 2/1.2 μm filter. The resulting fucoidan solution was analyzed for endotoxin by turbidimetric limulus amebocyte lysate (LAL) assay, and the concentration of moisture was analyzed with a moisture analyzer to determine the fucoidan content. The endotoxin level as endotoxin units per mg of fucoidan (EU/mg) of the fucoidan solution was found to be 1.7 EU/mg.

The fucoidan solution was then diafiltered with 5 mM NaCl over a single 100 kDa Tangential Flow Filtration (TFF) cassette under a batch-mode operation as follows: The fucoidan solution was first concentrated through volume reduction. An equivalent volume (1 diavolume) of 5 mM NaCl was then added to the fucoidan solution to initiate diafiltration. Concentration then diafiltration were repeated until 6 diavolumes of 5 mM NaCl had been introduced to the fucoidan solution. The diafiltered solution was concentrated to a final volume. The resulting retentate fucoidan composition was analyzed for endotoxin by turbidimetric LAL assay; and the concentration of moisture analyzed with a moisture analyzer to determine the fucoidan content. The endotoxin level was found to be reduced to 1.2 EU/mg.

Example 5. Tangential Flow Filtration

A starting fucoidan composition dissolved in deionized water was microfiltered through three different filters having progressively smaller pore size, with the last filter being a 2/1.2 μm filter. The resulting fucoidan solution was analyzed for endotoxin by turbidimetric limulus amebocyte lysate (LAL) assay, and the concentration of moisture was analyzed with a moisture analyzer to determine the fucoidan content. The endotoxin level as endotoxin units per mg of fucoidan (EU/mg) of the fucoidan solution was found to be 13,000 EU/mg.

The fucoidan solution was then diafiltered with 5 mM NaCl over a single 100 kDa Tangential Flow Filtration (TFF) cassette under a batch-mode operation as follows: The fucoidan solution was first concentrated through volume reduction. An equivalent volume (1 diavolume) of 5 mM NaCl was then added to the fucoidan solution to initiate diafiltration. Concentration then diafiltration were repeated until 8 diavolumes of 5 mM NaCl had been introduced to the fucoidan solution. The diafiltered solution was concentrated to a final volume. The resulting retentate fucoidan composition was analyzed for endotoxin by turbidimetric LAL assay; and the concentration of moisture analyzed with a moisture analyzer to determine the fucoidan content. The endotoxin level was found to be reduced to 6,100 EU/mg.

Example 6: Modified Tangential Flow Filtration

A crude fucoidan composition was first subjected to the physically induced flocculation method discussed in Example 2 to provide a starting fucoidan composition containing 109 EU/mg as determined by turbidimetric limulus amebocyte lysate (LAL) assay. This 109 EU/mg composition was then dissolved at 50 mg/ml in water and filtered through a 0.22 μm filter to obtain a starting solution. The starting solution was diafiltered for 7 diavolumes with a solution of 0.1 M NaOH, 0.01 M ethylene-diamine-tetraacetic acid (EDTA) and 0.01 M sodium dodecyl sulfate (SDS) to digest and remove biological contaminants and biological lysate components such as endotoxin. The SDS was removed from the resulting first retentate fucoidan composition outside of the assisted tangential flow filtration system by precipitation with 3 M potassium chloride followed by a centrifugation to remove precipitated potassium dodecyl sulfate. The resulting supernatant fucoidan composition was again diafiltered with 2 diavolumes of 0.01 M EDTA for the removal of residual SDS. The resulting secondary retentate fucoidan composition was analyzed for endotoxin by the turbidimetric LAL method and lyophilized to determine the fucoidan content. The endotoxin level of the fucoidan-low endotoxin composition was found to be less than 0.0006 EU/mg.

Example 7: Solid Phase Extraction

In two parallel experiments, two feedstock fucoidan compositions containing, respectively, about 4,000 and 8,000 endotoxin units per milligram (EU/mg) as measured by gel-clot LAL assay is added to 40° C. mixtures of 0.5 M NaOH in 70% v/v ethanol/water. The resulting reaction mixtures are stirred and maintained at 40° C. for 2 hours. The reaction mixtures are then centrifuged to separate the solid fucoidan-low endotoxin compositions from the 0.5 M NaOH in 70% v/v ethanol/water supernatant containing the extracted impurities.

After completion of the above process, the endotoxin level of the obtained fucoidan-low endotoxin compositions is measured by the gel-clot LAL assay and found to be 4 EU/mg and 8 EU/mg, respectively.

Example 8: Chemically Induced Precipitation

A feedstock fucoidan composition containing 33,006 EU/mg was prepared at 15% w/v in distilled water to obtain a starting solution. The starting solution was found to contain suspended particulates by observation. Calcium chloride was added to the starting solution to a level of 0.5 M to produce a reaction mixture. 10 M NaOH was added dropwise to the reaction mixture to bring the pH to between 7 and 8. This was done to avoid degradation of the fucoidan in the reaction mixture. A minimal amount of 10 M NaOH was again added to the reaction mixture to avoid the acidification of the reaction mixture from the subsequent addition of phosphoric acid. The reaction mixture was brought to 0.5 M phosphate through the addition of phosphoric acid. This initiated flocculation of the suspended particulates and precipitated impurities via the action of the calcium phosphate formed by the reaction of the calcium chloride with the phosphoric acid. The reaction mixture was allowed to stand at room temperature for 10 minutes to allow the flocculation to continue. The reaction mixture was centrifuged at 17,568 gravities for 17 minutes to separate the desired fucoidan-low endotoxin composition in a supernatant solution from the flocculated precipitate. The supernatant solution was lyophilized to obtain the fucoidan content and the fucoidan-low endotoxin composition was found to contain 27.7 endotoxin units per milligram of fucoidan (EU/mg) by turbidimetric LAL assay.

Example 9: Chemically Induced Precipitation

A feedstock fucoidan composition containing 33,006 EU/mg was prepared at 15% w/v in distilled water to obtain a starting solution. The starting solution was found to contain suspended particulates by observation. 10 M NaOH was added dropwise to the starting solution to bring the pH to between 7 and 8. This was done to avoid degradation of the fucoidan in the starting solution in case the subsequent addition of aluminum sulfate was to render the starting solution acidic. The starting solution was brought to 0.1 M aluminum sulfate to produce a reaction mixture. This initiated flocculation of the suspended particulates and precipitated impurities by the formed aluminum hydroxide. The reaction mixture was allowed to stand at room temperature for 10 minutes to allow the flocculation to continue. The reaction mixture was centrifuged at 17,568 gravities for 17 minutes to separate the desired fucoidan-low endotoxin composition in a supernatant solution from the flocculated precipitate. The supernatant solution was lyophilized to obtain the fucoidan content and the fucoidan-low endotoxin composition in the supernatant solution was found to contain 36.3 endotoxin units per milligram of fucoidan (EU/mg) by turbidimetric LAL assay.

Example 10: Lysis and Flocculation

An aqueous starting solution containing between 5 to 10% w/v of a starting fucoidan composition with endotoxin level at 25.9 endotoxin units per milligram of fucoidan (EU/mg) was provided. Solid tetrasodium EDTA was added as chelating agent to a concentration of 0.011 M. 1 M sodium dodecyl sulfate ("SDS") solution was added as cellular disrupting agent to a concentration of 0.011 M. 10 M NaOH solution was added to a concentration of 0.28 M to render the starting solution basic. The resulting reaction mixture was stirred for about 30 minutes at room temperature to afford a cloudy white mixture.

After about 30 minutes, 45% w/v KOH solution was added to a concentration of 0.07 M. The addition of potassium resulted in the precipitation of SDS and undesired impurities including endotoxins along with the SDS. 48% w/v aluminum sulfate solution was added to a concentration of 0.11 M. The formation of aluminum hydroxide flocculated undesired impurities including endotoxins in the reaction mixture. Sodium sulfite solid was added to a concentration of 0.02 M to quench potential oxidants in the reaction mixture.

The resulting reaction mixture was stored in a refrigerator for about 16 hours, followed by centrifugation at 17,568 gravities for 17 minutes to separate the desired fucoidan-low endotoxin composition in a supernatant solution from the flocculated impurities. The supernatant solution was lyophilized to obtain the fucoidan content and the fucoidan-low endotoxin composition in the supernatant solution was found to contain 0.02 endotoxin units per milligram of fucoidan (EU/mg) by turbidimetric LAL assay.

Example 11: Lysis and Flocculation

An aqueous starting solution containing between 5 to 10% w/v of a starting fucoidan composition with endotoxin level at 25.9 endotoxin units per milligram of fucoidan (EU/mg) was provided. Solid tetrasodium EDTA was added as chelating agent to a concentration of 0.033 M. 1 M sodium dodecyl sulfate (SDS) solution was added as cellular disrupting agent to a concentration of 0.033 M. 10 M NaOH solution was added to a concentration of 0.12 M to render the starting solution basic. The resulting reaction mixture was stirred for about 30 minutes at room temperature to afford a cloudy white mixture.

After about 30 minutes, 45% w/v KOH solution was added to a concentration of 0.07 M. The addition of potassium resulted in the precipitation of SDS and other impurities including endotoxins along with the SDS. 48% w/v aluminum sulfate solution was added to a concentration of 0.11 M. The formation of aluminum hydroxide flocculated undesired impurities including endotoxins in the reaction mixture. Sodium sulfite solid was added to a concentration of 0.02 M to quench any potential oxidants in the reaction mixture.

The resulting reaction mixture was stored at room temperature for about 16 hours, followed by centrifugation at 17,568 gravities for 17 minutes to separate the desired fucoidan-low endotoxin composition in a supernatant solution from the flocculated impurities. The supernatant solution was lyophilized to obtain a white solid, and the fucoidan content and the fucoidan-low endotoxin composition in the supernatant solution was found to contain less than 0.0005 endotoxin units per milligram of fucoidan (EU/mg) by turbidimetric LAL assay.

Example 12: Lysis and Flocculation

A feedstock fucoidan with endotoxin level at about 33,006 EU/mg was dissolved at about 10% w/v in boiling 0.1 M disodium phosphate to produce a reaction mixture. After 40 minutes at boiling temperature, the reaction mixture was centrifuged at 2300 gravities for 5 minutes to remove a portion of flocculated impurities including endotoxins. The resulting supernatant solution was brought to 50 mM trisodium phosphate with solid trisodium phosphate and 0.2 M NaOH with 10 M NaOH solution to render the supernatant solution basic. The resulting secondary reaction mixture was brought to 20 mM sodium metabisulfite by addition of solid sodium metabisulfite to quench any oxidants in the secondary reaction mixture. The secondary reaction mixture was brought to 10% EtOH by addition of 95% EtOH as a bacteriostatic agent. The secondary reaction mixture was brought to about 0.1% w/v benzalkonium chloride by addition of a solution of about 50% w/v benzalkonium chloride. The benzalkonium chloride was added to function as the cellular disrupting agent.

The secondary reaction mixture was stirred at room temperature for 1 hour, after which it was neutralized by addition of 6 M HCl. The secondary reaction mixture was brought to 0.15 M zinc chloride by addition of solid zinc chloride. The consequent formation of zinc phosphate flocculated undesired impurities in the secondary reaction mixture including endotoxins. The secondary reaction mixture of flocculants and solution was left to stir for another 15 minutes. The secondary reaction mixture was centrifuged at 2300 gravities for 5 minutes to separate the desired fucoidan in a second supernatant solution from the flocculated impurities. The resulting desired fucoidan-low endotoxin composition in the second supernatant solution was neutralized by addition of 10 M NaOH. The second supernatant solution was lyophilized to determine the fucoidan content and the fucoidan-low endotoxin composition in the second supernatant solution was found to have an endotoxin level of 2 EU/mg. The resulting second supernatant solution was diluted and subjected to TFF for the removal of benzalkonium chloride.

Example 13: Anionic Adsorption

A fucoidan composition was desalted over a 100 kDa TFF cassette to obtain a desalted fucoidan composition in a starting solution with an endotoxin level of 960 endotoxin units per milligram of fucoidan (EU/mg) as measured by the turbidimetric LAL method. A portion of the starting solution comprising about 500 mg of the desalted fucoidan composition was mixed with about 2.5 g Amberlyst A26 OH resin for about 16 hours. The liquid portion of the mixture was then separated from the resin by decanting. The liquid was lyophilized to obtain a fucoidan-low endotoxin composition found to contain 14.9 endotoxin units per milligram of fucoidan (EU/mg) by turbidimetric LAL assay.

Example 14: Anionic Adsorption

A fucoidan composition was desalted over a 100 kDa TFF cassette to obtain a desalted fucoidan composition in a starting solution with an endotoxin level of 960 endotoxin units per milligram of fucoidan (EU/mg) as measured by the turbidimetric LAL method. A portion of the starting solution comprising about 500 mg of the desalted fucoidan composition was mixed with about 5.0 g Amberlyst A26 OH resin for about 16 hours. The liquid portion of the mixture was then separated from the resin by decanting. The liquid was lyophilized to obtain a fucoidan-low endotoxin composition found to contain 0.06 endotoxin units per milligram of fucoidan (EU/mg) by turbidimetric LAL assay.

Example 15: Anionic Adsorption

A fucoidan composition was desalted over a 100 kDa TFF cassette to obtain a desalted fucoidan composition in a starting solution with an endotoxin level of 960 endotoxin units per milligram of fucoidan (EU/mg) as measured by the turbidimetric LAL method. A portion of the starting solution comprising about 500 mg of the desalted fucoidan composition was mixed with Triton® X100 to a final concentration of about 0.5 mM. The resulting solution was mixed with about 2.5 g Amberlyst A26 OH resin for about 16 hours. The liquid portion of the mixture was then separated from the resin by decanting. The liquid was lyophilized to obtain a fucoidan-low endotoxin composition found to contain less than 0.003 endotoxin units per milligram of fucoidan (EU/mg) by turbidimetric LAL assay.

Example 16: Anionic Adsorption

A fucoidan composition was desalted over a 100 kDa TFF cassette to obtain a desalted fucoidan composition in a starting solution with an endotoxin level of 960 endotoxin units per milligram of fucoidan (EU/mg) as measured by the turbidimetric LAL method. A portion of the starting solution comprising about 500 mg of the desalted fucoidan composition was mixed with n-butanol to a final concentration of about 5% v/v. The resulting solution was mixed with about 2.5 g Amberlyst A26 OH resin for about 16 hours. The liquid portion of the mixture was then separated from the resin by decanting. The liquid was lyophilized to obtain a fucoidan-low endotoxin composition found to contain 6.7 endotoxin units per milligram of fucoidan (EU/mg) by turbidimetric LAL assay.

Example 17: Anionic Adsorption

A fucoidan composition was desalted over a 100 kDa TFF cassette to obtain a desalted fucoidan composition in a starting solution with an endotoxin level of 960 endotoxin units per milligram of fucoidan (EU/mg) as measured by the turbidimetric LAL method. A portion of the starting solution comprising about 500 mg of the desalted fucoidan composition was mixed with ethanol to a final concentration of 10% v/v. The resulting solution was mixed with about 2.5 g Amberlyst A26 OH resin for about 16 hours. The liquid portion of the mixture was then separated from the resin by decanting. The liquid was lyophilized to obtain a fucoidan-low endotoxin composition found to contain 6.0 endotoxin units per milligram of fucoidan (EU/mg) by turbidimetric LAL assay.

Example 18: Liquid-Liquid Extraction

A starting fucan composition containing about 10,000 EU/mg is dissolved at 10 mg/mL in distilled water to produce an aqueous starting solution. 20% v/v heptane is added to the aqueous starting solution containing the starting fucoidan composition and the organic-aqueous mixture is then mixed at high shear for 30 minutes. The mixing is terminated, and the organic-aqueous mixture placed in a separatory funnel for the separation of the organic phase from the aqueous phase. The denser aqueous phase containing the desired fucan component settles to the bottom of the separatory funnel while the less dense organic phase containing undesired impurities is present at the upper end of the separatory funnel. The organic-aqueous mixture is allowed to sit in the separatory funnel for 10 minutes. The aqueous phase is then decanted and collected as the desired fucan-low endotoxin composition in solution. The fucan-low endotoxin composition in solution may be found to contain between about 50% to about 99.999% less endotoxin than the starting fucan composition by the turbidimetric LAL method.

Example 19: Liquid-Liquid Extraction

A starting fucan composition containing about 10,000 EU/mg is dissolved at 10 mg/mL in distilled water to produce an aqueous starting solution. 20% v/v 1-butanol is added to the aqueous starting solution containing the starting fucoidan composition and the organic-aqueous mixture is then mixed at high shear for 30 minutes. The mixing is terminated, and the organic-aqueous mixture placed in a separatory funnel for the separation of the organic phase from the aqueous phase. The denser aqueous phase containing the desired fucan component settles to the bottom of the separatory funnel while the less dense organic phase containing undesired impurities is present at the upper end of the separatory funnel. The organic-aqueous mixture is allowed to sit in the separatory funnel for 10 minutes. The aqueous phase is then decanted and collected as the desired fucan-low endotoxin composition in solution. The fucan-low endotoxin composition in solution may be found to contain between about 50% to about 99.999% less endotoxin than the starting fucan composition by the turbidimetric LAL method.

Example 20: Liquid-Liquid Extraction

A starting fucan composition containing about 10,000 EU/mg is dissolved at 10 mg/mL in distilled water to produce an aqueous starting solution. 20% v/v ethyl acetate is added to the aqueous starting solution containing the starting fucoidan composition and the organic-aqueous mixture is then mixed at high shear for 30 minutes. The mixing is terminated, and the organic-aqueous mixture placed in a separatory funnel for the separation of the organic phase from the aqueous phase. The denser aqueous phase containing the desired fucan component settles to the bottom of the separatory funnel while the less dense organic phase containing undesired impurities is present at the upper end of the separatory funnel. The organic-aqueous mixture is allowed to sit in the separatory funnel for 10 minutes. The aqueous phase is then decanted and collected as the desired fucan-low endotoxin composition in solution. The fucan-low endotoxin composition in solution may be found to contain between about 50% to about 99.999% less endotoxin than the starting fucan composition by the turbidimetric LAL method.

Example 21: Endotoxin Determination of Crude Fucans Used to Make Certain Fucans Discussed in Some of the Following Examples Crude fucans used to make certain fucans discussed in following examples. In particular, the Crude fucans used to make fucan 2, fucan 4, and fucan 7 were analyzed for endotoxin by limulus amebocyte lysate (LAL) assay. "Crude fucan 1" refers to the crude fucan that was used to make fucan 2 and also used to make fucan 4. "Crude fucan 2" and "crude fucan 3" refer to two crude fucans that were blended together and then used to make fucan 7. The results of such analyses are shown in Table 1. Results in the tables below contain abbreviations used for certain characteristics of endotoxin. Endotoxin units per milligram is denoted by EU/mg.

TABLE 1

| | Endotoxin analysis results (EU/mg) |
|---|---|
| Crude fucan 1 | 6,627 |
| Crude fucan 2 | 31,712 |
| Crude fucan 3 | 33,006 |

Example 22: Preparation of Fucan-Low Endotoxin Compositions

The methods discussed herein may be used, combined, modified and permuted in any manner to obtain fucan-low endotoxin compositions. Ten fucan-low endotoxin compositions were prepared from high-endotoxin (e.g., feedstock) fucan compositions to evaluate the efficacy of fucan-low endotoxin compositions in medical and surgical applications. More particularly, high-endotoxin fucan compositions with endotoxin levels ranging from 10,000 EU/mg to 60,000 EU/mg were modified and/or depyrogenated using one or more of the methods herein to obtain the ten fucan-low endotoxin compositions. The ten fucan-low endotoxin compositions are hereafter referred to as fucan 1 to fucan 10. Fucan 1 to fucan 6, fucan 8 and fucan 10 were white solids. Fucan 9 was a light brown solid. Fucan 7 was dissolved in solution to obtain a clear-colorless solution. The preparation of fucan 1, fucan 3 and fucan 7 involved using a combination of methods discussed in example 8 and example 10 plus further diafiltration against a low ionic strength solution. The preparation of fucan 2 and fucan 4 involved using a combination of the methods discussed in example 7, micellar phase separation and example 15. The preparation of fucan 9 involved using a combination of the methods discussed in example 7, micellar phase separation and tangential flow filtration against deionized water. The preparation of fucan 6, fucan 8 and fucan 10 involved using a combination of the methods discussed in example 9 and example 10 plus further diafiltration against a low ionic strength solution. The endotoxin levels, molecular weights, sulfate levels and total carbohydrate levels were determined as follows.

Example 23: Measurement of Endotoxins and Molecular Weights of Desired Fucan-Low Endotoxin Compositions For fucans 1 to 8 and fucan 10, turbidimetric endotoxin testing was carried out using Associates of Cape Cod Pyrotell®-T lysate in accordance with manufacturer's instructions. Turbidity measurements were taken using a Biotek Synergy® HTX incubating plate reader. Results were quantified against manufacturer CSE (control standard endotoxin) calibration curves.

For fucan 9, chromogenic endotoxin testing was carried out using a Charles River Nexgen®-PTS spectrophotometer using Charles River Endosafe® cartridges. Results were quantified against manufacturer CSE (control standard endotoxin) calibration curves.

Results for endotoxin testing of fucan 1 to fucan 10 are shown in Table 2 below.

TABLE 2 endotoxin results of 10 different fucans

| | Endotoxin (EU/mg) |
|---|---|
| Fucan 1 | 0.180 |
| Fucan 2 | 0.044 |
| Fucan 3 | 0.090 |
| Fucan 4 | 0.020 |
| Fucan 5 | 0.007 |
| Fucan 6 | 0.007 |
| Fucan 7 | 0.002 |
| Fucan 8 | 0.030 |
| Fucan 9 | 0.180 |
| Fucan 10 | 0.001 |

Table 2 demonstrates that fucan-low endotoxin compositions have been produced with endotoxin levels ranging from 0.001 to 0.18 EU/mg.

Example 24: Molecular Weight Distribution, Sulfate, Total Carbohydrate and Monosaccharide Composition Analysis of Fucan-Low Endotoxin Compositions Gel permeation chromatography (GPC) was used to measure the molecular weight distributions of the fucan-low endotoxin compositions fucan 1, fucan 2, fucan 4, fucan 5, fucan 6, fucan 8 and fucan 10. There are a large number of different parameters, columns and standards available for use in gel permeation chromatography, resulting in a variety of instrumentation set-ups available for the analysis of molecular weight. For molecular weight determinations herein, the GPC were conducted using the following parameters: The mobile phase was 0.1 M sodium nitrate run at 0.6 mL/min. The column compartment and detector were at 30° C. A Waters 2414 refractive index detector was used for detection.

Suitable GPC columns include GPC columns compatible with aqueous solvents, for example, columns packed with at least one of sulfonated styrene-divinylbenzene, NH-functionalized acrylate copolymer network, modified silica and hydroxylated polymethacrylate-based gel. For the analyses herein, three columns were used in series, comprising one 40 mm long guard column with an inner diameter (ID) of 6 mm packed with 6 μm particle size hydroxylated polymethacrylate-based gel, followed by a first 300 mm analytical GPC column with a 7.8 mm ID packed with 12 μm particle size hydroxylated polymethacrylate-based gel that has an exclusion limit of about 7,000 kDa and an effective molecular weight range of between about 50 kDa and about 5,000 kDa, followed by a second 300 mm analytical GPC column with a 7.8 mm ID packed with 10 μm particle size hydroxylated polymethacrylate-based gel that has an exclusion limit of about 7,000 kDa and an effective molecular weight range of between about 1 kDa and about 6,000 kDa. The total effective molecular weight range of the column set up was between about 1 kDa and about 6,000 kDa. An example of this column set up can be Ultrahydrogel® guard-Ultrahydrogel® 2000-Ultrahydrogel® Linear columns connected in series.

Samples run were quantified against a standard curve comprising of traceable standards from the American Polymer Standards Corporation: DXT3755K (peak molecular weight=2164 kDa), DXT820K (peak molecular weight=745 kDa), DXT760K (peak molecular weight=621 kDa), DXT670K (peak molecular weight=401 kDa), DXT530K (peak molecular weight=490 kDa), DXT500K (peak molecular weight=390 kDa), DXT270K (peak molecular weight=196 kDa), DXT225K (peak molecular weight=213 kDa), DXT150K (peak molecular weight=124 kDa), DXT55K (peak molecular weight=50 kDa), DXT50K (peak molecular weight=44 kDa) and DXT5K (peak molecular weight=4 kDa), the peak molecular weights of these standards being between about 4 kDa and about 2,200 kDa. The standard curve used may, for example, include Dextran 3755 kDa, at least one of Dextran 50 kDa and Dextran 55 kDa, and between 3 to 6 additional traceable standards discussed herein, the calibration points being the peak molecular weights of the calibrants used. An example calibration curve may consist of DXT3755K, DXT 820K, DXT530K, DXT500K, DXT225K and DXT55K. The columns used herein had a total effective molecular weight range that encompassed and extended beyond the peak molecular weight range of the standards used for quantification of the fucans.

Results in Table 3 below contain abbreviations used for certain characteristics of a molecular weight distribution. Gel permeation chromatography is denoted by GPC, peak molecular weight is denoted by PMW, weight average molecular weight is denoted by WAMW, number average molecular weight is denoted by NAMW, percentage distribution is denoted by % dist. and molecular weight is denoted by MW.

TABLE 3

Molecular weight and endotoxin characteristics of seven fucan-low endotoxin compositions

| | PMW (kDa) | WAMW (kDa) | NAMW (kDa) | % dist. >100 kDa | % dist. >200 kDa | % dist. >500 kDa | % dist. >1600 kDa |
|---|---|---|---|---|---|---|---|
| Fucan 1 | 409.39 | 772.00 | 291.78 | 93.96 | 81.49 | 43.51 | 9.76 |
| Fucan 2 | 107.12 | 136.05 | 79.86 | 53.43 | 19.83 | 1.10 | 0.00 |
| Fucan 4 | 612.33 | 856.96 | 448.71 | 98.55 | 92.43 | 61.37 | 12.01 |
| Fucan 5 | 457.33 | 592.80 | 300.92 | 95.39 | 82.93 | 43.84 | 4.93 |
| Fucan 6 | 807.23 | 1233.04 | 713.99 | 99.91 | 98.52 | 79.66 | 23.60 |
| Fucan 8 | 686.21 | 1876.74 | 524.89 | 98.37 | 92.97 | 69.90 | 30.60 |
| Fucan 10 | 686.12 | 1083.48 | 604.43 | 99.75 | 97.24 | 72.32 | 18.86 |

The fucan-low endotoxin compositions shown in Table 2 may be further characterized by their molecular weight distribution, shown in Table 3. Fucan-low endotoxin compositions with a peak molecular weight between about 100 kDa and about 850 kDa, a weight average molecular weight between about 130 kDa and 2000 kDa, a number average molecular weight between about 80 kDa and 750 kDa and at least 50% of the distribution above 100 kDa have been prepared.

Fucan-low endotoxin compositions fucan 1, fucan 2, fucan 4, fucan 5, fucan 6, fucan 7, fucan 8 and fucan 10 were dissolved in deionized water, hydrolyzed under acidic conditions and analyzed by inductively coupled plasma mass spectrometry (ICP-MS) for % w/w total sulfur content, performed by ALS Environmental laboratories in Burnaby, British Columbia. Sulfur content was converted to sulfate content by multiplying the sulfur content by the molar ratio of sulfate to sulfur to obtain % w/w sulfate content of the fucan composition. The sulfate contents of the fucan-low endotoxin compositions are shown in table 4 below.

Fucan-low endotoxin compositions fucan 1, fucan 2, fucan 4, fucan 5, fucan 6 fucan 7, fucan 8 and fucan 10 were also analyzed for total carbohydrate and monosaccharide composition. Fucan-low endotoxin compositions were dissolved in 72% w/w sulfuric acid at 40 mg/mL and incubated at 45° C. in a water bath for 30 minutes. The acid hydrolysate was then diluted to 4% w/w sulfuric acid in a high-pressure tube and incubated at 120° C. for 60 minutes. The resulting second acid hydrolysate was diluted to a 1/333 concentration with distilled water and run on high performance anionic exchange column chromatography set up with pulsed amperometry detection. Separation of analytes was accomplished over a Carbopac® PA20 analytical column by running 10 mM NaOH eluent at 1.0 mL/minute using an isocratic pump.

The fucan-low endotoxin compositions were found to contain fucose and galactose. The total carbohydrate content was determined by the sum total of analytes measured. The fucose contents of the fucan-low endotoxin compositions were determined by interpolation on a standard curve for fucose. The galactose content of the fucan-low endotoxin compositions were determined by the method of standard addition. The total carbohydrate content and fucose and galactose contents as percentages of the total carbohydrate content for the fucan-low endotoxin compositions are shown in Table 4 below. Carbohydrate in the Table below is abbreviated “carb”.

TABLE 4

Sulfate content, carbohydrate content and monosaccharide composition of fucan-low endotoxin compositions

| | Sulfate content (% w/w of the fucan) | Total carb. content (% w/w of the fucan) | Fucose (% w/w of the total carb. content) | Galactose (% w/w of total carb. content) |
|---|---|---|---|---|
| Fucan 1 | 39.8 | 50.0 | 56.5 | 43.5 |
| Fucan 2 | 32.2 | 29.9 | 90.8 | 9.2 |
| Fucan 4 | 34.3 | 35.1 | 90.5 | 9.5 |
| Fucan 5 | 44.9 | 41.7 | 89.7 | 10.3 |
| Fucan 6 | 51.6 | 47.8 | 91.0 | 9.0 |
| Fucan 7 | 44.9 | 53.5 | 93.9 | 6.1 |
| Fucan 8 | 51.3 | 49.3 | 92.3 | 7.7 |
| Fucan 10 | 44.8 | 59.0 | 89.9 | 10.2 |

Example 25: Epidural Fibrous Adhesion Treatment

Fucoidan solutions made from fucan-low endotoxin compositions fucan 1, fucan 2, fucan 4 and fucan 5 shown in Tables 2 to 4 were prepared at 100 mg/mL in Lactated Ringer’s Injection USP (LRS). Fucan 8 was prepared at 500 mg/mL in Lactated Ringer’s Injection USP (LRS). Laminectomy surgery was performed on Sprague Dawley rats, the average weights of the rats and the dose in milligram per kilogram shown in Table 5 below. A line block along the lumbar spine was created with bupivacaine solution. The back of the rat was cleaned and then covered with sterile drapes. The lumbar fascia was opened through a midline skin incision, lumbosacral fascia was incised and the paralumbar muscles were dissected to expose the underlying vertebral laminae. Bone at the center of the vertebrae was removed. Throughout the procedure, haemostasis was maintained by irrigation with Lactated Ringer's Injection USP (LRS) and pressure with cotton swabs. The exposed dura was treated directly with 15 microliters of LRS (control) or fucoidan solution. The muscle and skin layers were closed with sutures and the rats were allowed to recover for one week before sacrifice for adhesion quantification. The presence and size of adhesions on the dura were noted. The dimensions of the adhesions and the exposed dura were recorded and used to calculate adhesion coverage percentage, being the adhesion area as a percentage of the total exposed dura area:

$$\text{Adhesion coverage (\%)} = 100 \times \text{dura adhesion area } (\text{mm}^2) \div \text{total exposed dura area } (\text{mm}^2) \quad \text{Equation 1}$$

The control group receiving LRS was determined to have a 65% adhesion coverage using equation 1. The adhesion coverage for the fucan-low endotoxin compositions fucan 1, fucan 2, fucan 4 and fucan 5 are shown in Table 5 below with the reduction in adhesion coverage relative to the control group.

TABLE 5

Reduction in Rat Epidural Adhesion relative to control LRS using five different fucans

| | Average Rat Weight (kg) | Dose (mg) | Dose per animal weight (mg/kg) | Number of Rats Scored | % Reduction in Epidural Adhesion vs. Control |
|---|---|---|---|---|---|
| Fucan 1 | 0.50 | 1.5 | 3.0 | 2 | 100% |
| Fucan 2 | 0.65 | 1.5 | 2.3 | 4 | 83% |
| Fucan 4 | 0.64 | 1.5 | 2.3 | 4 | 100% |
| Fucan 5 | 0.58 | 1.5 | 2.6 | 2 | 100% |
| Fucan 8 | 0.59 | 7.5 | 12.8 | 3 | 100% |

As may be seen in Table 5, fucan-low endotoxin compositions can be used to successfully inhibit, prevent, remove, reduce, or otherwise treat post-surgical adhesions.

Example 26: Uterine horn fibrous adhesion treated with fucan 7

To determine the efficacy of the low endotoxin fucan 7 composition in inhibiting surgical adhesions, the following double uterine horn (DUH) surgeries were performed on both horns of a total of four New Zealand White rabbits. Prior to surgery, the rabbits were weighed and then prepared for surgery by premedication with ketamine and xylazine.

Fucoidan solution was prepared at 0.33 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. 15 mL/kg fucoidan solution per rabbit weight was applied to the abdominal cavity, directing about half of the fucoidan solution towards the left horn and about half of the fucoidan solution towards the right horn, before the incision was closed. Adhesion formation was evaluated two weeks after the surgery. Horns with detached sutures were not evaluated. Length of the uterine horn adhesion was measured with a ruler. The uterine horn adhesion coverage percentage, being the length of the adhesion as a percentage of the total damaged uterine horn length was calculated as:

$$\text{Adhesion coverage (\%)} = 100 \times \text{uterine horn adhesion length} \div \text{total damaged uterine horn length} \quad \text{Equation 2}$$

The same surgical method was applied to four New Zealand White rabbits, receiving 15 mL/kg of control Lactated Ringer's Injection USP (LRS) instead of fucoidan solution.

The control group receiving LRS was determined to have a 63% adhesion coverage using equation 2. Table 6 shows the results obtained using the method discussed above for fucan 7 composition, being a representative example of a fucan-low endotoxin composition. The results in Table 6 below are shown as the reduction in adhesion coverage relative to the control group.

Table 6 provides the results of treating six uterine horns with fucan 7.

TABLE 6

Reduction in rabbit uterine horn adhesion using fucan 7 relative to control LRS

| | Dose (mg/kg) | Number of Uterine Horns | % Reduction in uterine horn adhesion coverage vs. control |
|---|---|---|---|
| Fucan 7 | 5 | 6 | 100% (i.e., 100.0% reduction in fibrous adhesions compared to control) |

As may be seen from the results of Table 6, fucan-low endotoxin compositions may be used to successfully inhibit, prevent, remove, reduce, or otherwise treat post-surgical uterine horn adhesions.

Example 27: Uterine Horn Fibrous Adhesion Treated With Fucan 8

To determine the efficacy of the low endotoxin fucan 8 composition in inhibiting surgical adhesions, the following double uterine horn (DUH) surgeries were performed on both horns of a total of four New Zealand White rabbits. Prior to surgery, the rabbits were weighed and then prepared for surgery by premedication with ketamine and xylazine.

Fucoidan solution was prepared at 3.75 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns were also scraped. A volume of 4 mL of fucoidan solution was applied directly to the left injured uterine horn and sidewall area and 4 mL of fucoidan solution was applied directly to the right injured uterine horn and sidewall area. The damaged uterine horns and abdominal wall were placed next to each other and stabilized with sutures. A drainage tube was positioned in the peritoneal cavity before the incision was closed. The drainage tube was removed 48 h post-surgery. Adhesion was evaluated two weeks after the surgery. Length of the uterine horn adhesion was measured with a ruler. The uterine horn adhesion coverage was calculated using equation 2.

The same surgical method was applied to 3 New Zealand White rabbits, receiving 4 mL per side of control Lactated Ringer's Injection USP (LRS) instead of fucoidan solution. The control group receiving LRS was determined to have a 73% adhesion coverage using equation 2. Table 7 shows the results obtained using the method discussed above for fucan 8 composition, being a representative example of a fucan-low endotoxin composition. The results in the Table below are shown as the reduction in adhesion coverage relative to the control group.

Table 7 provides the result of treating eight uterine horns with fucan 8.

TABLE 7

Reduction in rabbit uterine horn adhesion using fucan 8 relative to control LRS

| | Dose (mg/kg) | Number of Uterine Horns | % Reduction in uterine horn adhesion coverage vs. control |
|---|---|---|---|
| Fucan 8 | 9.8 | 8 | 92.9% |

As may be seen from the results of Table 7, fucan-low endotoxin compositions may be used to successfully inhibit, prevent, remove, reduce, or otherwise treat post-surgical uterine horn adhesions.

Example 28: Uterine Horn Fibrous Adhesion Treated With Fucan 9

To determine the efficacy of the low endotoxin fucan 9 composition in inhibiting surgical adhesions, the following double uterine horn (DUH) surgeries were performed on both horns of a total of nine New Zealand White rabbits. Prior to surgery, the rabbits were weighed and then prepared for surgery by premedication with ketamine and xylazine.

Fucoidan solution was prepared at 0.17 mg/mL, 0.33 mg/mL and 0.67 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. 15 mL/kg fucoidan solution per rabbit weight was applied to the abdominal cavity before the incision was closed. Adhesion was evaluated two weeks after the surgery. Three rabbits were evaluated at each fucoidan concentration prepared. Length of the uterine horn adhesion was measured with a ruler. The uterine horn adhesion length was calculated using equation 2.

The same surgical method was applied to 3 New Zealand White rabbits, receiving about 48 mL (about 15 mL/kg) of control Lactated Ringer's Injection USP (LRS) instead of fucoidan solution. The control group receiving LRS was determined to have a 54% adhesion coverage using equation 2. Table 8 shows the results obtained using the method discussed above for fucan 9 composition at different doses, being a representative example of a fucan-low endotoxin composition. The results in the Table below are shown as the reduction in adhesion coverage relative to the control group.

Table 8 provides the result of treating eighteen uterine horns with fucan 9.

TABLE 8

Reduction in rabbit uterine horn adhesion using fucan 9 relative to control LRS

| | Concentration in Lactated Ringer's Injection USP (mg/mL) | Dose (mg/kg) | Number of Uterine Horns | % Reduction in uterine horn adhesion coverage vs. control |
|---|---|---|---|---|
| Fucan 9 | 0.17 | 2.5 | 6 | 100% |
| Fucan 9 | 0.33 | 5 | 6 | 100% |
| Fucan 9 | 0.67 | 10 | 6 | 100% |

As may be seen from the results of Table 8, fucan-low endotoxin compositions may be used to successfully inhibit, prevent, remove, reduce, or otherwise treat post-surgical uterine horn adhesions.

Example 29: Uterine Horn Adhesions Treated With Fucan 8

To determine the efficacy of the low endotoxin fucan 8 composition in inhibiting surgical adhesions, the following double uterine horn (DUH) surgeries were performed on both horns of a total of three New Zealand White rabbits. Prior to surgery, the rabbits were weighed and then prepared for surgery by premedication with ketamine and xylazine.

Fucoidan solution was prepared at 5 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. The top third and the bottom third of the muscle incision was closed and 5 mL/kg fucoidan solution per rabbit weight was applied to the abdominal cavity. The muscle incision was temporarily closed and the fucoidan solution left in the abdominal cavity for 30 minutes. The muscle incision was reopened and the abdominal cavity was flushed with 10 mL/kg LRS. The majority of the fluid in the abdominal cavity was suctioned out before the incision was closed. Adhesion formation was evaluated two weeks after the surgery. Length of the uterine horn adhesion was measured with a ruler. The uterine horn adhesion coverage percentage, being the length of the adhesion as a percentage of the total damaged uterine horn length was calculated using equation 2.

Table 9 shows the results obtained using the method discussed above for fucan 8 composition, being a representative example of a fucan-low endotoxin composition. The results in the Table below are shown as the mean adhesion length across the 6 uterine horns scored.

TABLE 9

Adhesion length using fucan 8

| | Dose (mg/kg) | Number of Uterine Horns | Mean % adhesion length |
|---|---|---|---|
| Fucan 8 | 25 | 6 | 0% (i.e., no adhesions were found) |

As may be seen from the results of Table 9, fucan-low endotoxin compositions may be used to successfully inhibit, prevent, remove, reduce, or otherwise treat post-surgical uterine horn adhesions.

Example 30: Uterine Horn Fibrous Adhesion Treated With A Fucan-Low Endotoxin Composition To determine the efficacy of a fucan-low endotoxin composition comprising a total endotoxin level of 0.003 EU/mg in inhibiting surgical adhesions, the following double uterine horn (DUH) surgeries were performed on both horns of a total of twenty New Zealand White rabbits. Prior to surgery, the rabbits were weighed and then prepared for surgery by premedication with midazolam and dexmedetomidine.

Fucoidan solution was prepared at each concentration of 0.02 mg/mL, 0.1 mg/mL, 0.5 mg/mL, or 2.5 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. About 2 mL/kg fucoidan solution per rabbit weight was applied to the abdominal cavity before the incision was closed. Adhesion was evaluated two weeks after the surgery. Five rabbits were treated and evaluated for each fucoidan concentration prepared. Length of the uterine horn adhesion was measured with a ruler. The uterine horn adhesion length was calculated using equation 2.

The same surgical method was applied to 5 additional New Zealand White rabbits for control, each receiving about 2 mL/kg of control Lactated Ringer's Injection USP (LRS) instead of fucoidan solution. The control group receiving LRS was determined to have a 100% adhesion coverage using equation 2. Table 10 shows the results obtained using the method discussed above for the fucan-low endotoxin composition at different concentrations and dosages (in total forty uterine horns were treated with fucan solution, 10 each for each concentration of the fucan-low endotoxin composition); the results are shown as the reduction in adhesion coverage relative to the control group.

TABLE 10

Decrease in rabbit uterine horn adhesion using a fucan-low endotoxin composition relative to control LRS

| Concentration (mg/mL) | Dose (mg/kg) | Number of Uterine Horns | % Reduction in uterine horn adhesion coverage vs. control |
|---|---|---|---|
| 0.02 | 0.04 | 10 | 10% (i.e., 10% decrease in fibrous adhesions compared to control) |
| 0.1 | 0.2 | 10 | 30% (i.e., 30% decrease in fibrous adhesions compared to control) |
| 0.5 | 1 | 10 | 71% (i.e., 71% decrease in fibrous adhesions compared to control) |
| 2.5 | 5 | 10 | 95% (i.e., 95% decrease in fibrous adhesions compared to control) |

As can be seen from the results of Table 10, fucan-low endotoxin compositions can be used to successfully inhibit, prevent, remove, reduce, or otherwise treat post-surgical uterine horn adhesions.

REFERENCE NUMERAL LIST

1000 Modified TFF system
1002 Input supply line
1004 Pre-filter
1006 TFF system output valve
1008 Assisted TFF system output line
1010 Tangential flow filtration (TFF) filter
1012 TFF supply line
1014 TFF input pump
1016 Fucan container
1017 TFF retentate valve
1018 TFF retentate return line
1019 TFF permeate output line
1020 First diafiltration solution container
1024 First diafiltration solution valve
1025 First diafiltration solution supply line
1030 Second diafiltration solution container
1034 Second diafiltration solution valve
1035 Second diafiltration solution supply line
1400 Anionic adsorption endotoxin removal system
1401 Input supply line
1402 Inter-subsystem valve
1403 TFF subsystem retentate output line
1404 Anion exchange subsystem output valve
1405 Anion exchange subsystem output line 1406 Pre-filter
1406 Pre-filter
1410 Tangential flow filtration (TFF) subsystem
1411 Tangential flow filtration (TFF) filter
1412 TFF filter supply line
1413 Diafiltration solution valve
1414 TFF subsystem pump
1415 TFF subsystem diafiltration solution supply line
1416 TFF subsystem fucan container
1417 TFF subsystem diafiltration solution container
1418 TFF subsystem retentate return line
1419 TFF subsystem permeate output line
1420 Anion exchange subsystem
1421 Anion exchange vessel
1422 Anion exchange vessel supply line
1424 Anion exchange subsystem pump
1425 Disrupting agent supply line
1426 Anion exchange subsystem fucan container
1427 Disrupting agent container
1428 Anion exchange vessel output line
1429 Macroporous anion exchange resin All terms used herein are used in accordance with their ordinary meanings unless the context or definition clearly indicates otherwise. Also unless expressly indicated otherwise, in this disclosure the use of "or" includes "and" and vice-versa. Non-limiting terms are not to be construed as limiting unless expressly stated, or the context clearly indicates, otherwise (for example, "including," "having," and "comprising" typically indicate "including without limitation"). Singular forms, including in the claims, such as "a," "an," and "the" include the plural reference unless expressly stated, or the context clearly indicates otherwise.

Unless otherwise indicated, adjectives herein such as "substantially" and "about" that modify a condition or relationship characteristic of a feature or features of an embodiment, indicate that the condition or characteristic is defined to within tolerances that are acceptable for operation of the embodiment for an application for which it is intended.

The scope of the present methods, compositions, systems, etc., includes both means plus function and step plus function concepts. However, the claims are not to be interpreted as indicating a "means plus function" relationship unless the word "means" is specifically recited in a claim, and are to be interpreted as indicating a "means plus function" relationship where the word "means" is specifically recited in a claim. Similarly, the claims are not to be interpreted as indicating a "step plus function" relationship unless the word "step" is specifically recited in a claim, and are to be interpreted as indicating a "step plus function" relationship where the word "step" is specifically recited in a claim.

From the foregoing, it will be appreciated that, although specific embodiments have been discussed herein for purposes of illustration, various modifications may be made without deviating from the spirit and scope of the discussion herein. Accordingly, the systems and methods, etc., include such modifications as well as all permutations and combinations of the subject matter set forth herein and are not limited except as by the appended claims or other claim having adequate support in the discussion and figures herein.

What is claimed is:

1. A fucan-low endotoxin composition comprising less than about 0.2 endotoxin units per milligram of the fucan, and wherein the fucan has a sulfation level of between about 20% w/w and 60% w/w.

2. The fucan-low endotoxin composition of claim 1 wherein the fucan-low endotoxin composition comprises less than about 0.1 endotoxin units per milligram of the fucan.

3. A fucan-low endotoxin composition comprising less than about 0.2 endotoxin units per milligram of the fucan, wherein the fucan-low endotoxin composition comprises less than about 0.03 endotoxin units per milligram of the fucan.

4. A fucan-low endotoxin composition comprising less than about 0.2 endotoxin units per milligram of the fucan, wherein the fucan-low endotoxin composition comprises less than about 0.003 endotoxin units per milligram of the fucan.

5. The fucan-low endotoxin composition of any one of claims 1, 3 and 4, wherein the fucan has a molecular weight distribution wherein at least 60% w/w of the distribution is greater than 100 kDa when measured using an aqueous gel permeation chromatography set up consisting essentially of:

one 300 mm analytical gel permeation chromatography column with a 7.8 mm inner diameter packed with hydroxylated polymethacrylate-based gel, having an effective molecular weight range of between about 50 kDa and about 5,000 kDa, one 300 mm analytical gel permeation chromatography column with a 7.8 mm inner diameter packed with hydroxylated polymethacrylate-based gel, having an effective molecular weight range of between about 1 kDa and about 6,000 kDa and one 40 mm guard column with a 6 mm inner diameter packed with hydroxylated polymethacrylate-based gel, the two analytical gel permeation chromatography columns and the one guard column contained in a column compartment at about 30° C.;

a refractive index detector at about 30° C.;

0.1M sodium nitrate mobile phase run at 0.6 mL/min; and quantification against a peak molecular weight standard curve consisting essentially of a first dextran standard with a peak molecular weight of about 2,200 kDa, a second dextran standard with a peak molecular weight of between about 720 kDa and about 760 kDa, a third dextran standard with a peak molecular weight between about 470 kDa and about 510 kDa, a fourth dextran standard with a peak molecular weight between about 370 kDa and about 410 kDa, a fifth dextran standard with a peak molecular weight between about 180 kDa and about 220 kDa, and a sixth dextran standard with a peak molecular weight between about 40 kDa and 55 kDa.

6. The fucan-low endotoxin composition of claim 5, wherein the fucan has a molecular weight distribution wherein at least 81% w/w of the distribution is greater than 200 kDa.

7. The fucan-low endotoxin composition of claim 5, wherein the fucan has a molecular weight distribution wherein at least 44% w/w of the distribution is greater than 500 kDa.

8. The fucan-low endotoxin composition of claim 5, wherein the fucan has a molecular weight distribution wherein at least 5% w/w of the distribution is greater than 1600 kDa.

9. The fucan-low endotoxin composition of claim 5, wherein the fucan has a weight average molecular weight greater than 100 kDa.

10. The fucan-low endotoxin composition of any one of claims 1, 3, and 4, wherein the fucan has a total carbohydrate content of between 27% w/w and 80% w/w.

11. The fucan-low endotoxin composition of claim 10, wherein the fucan has a total fucose content as a percentage of the total carbohydrate content of at least about 30% w/w.

12. The fucan-low endotoxin composition of claim 10, wherein the fucan has a total galactose content as a percentage of the total carbohydrate content below about 60% w/w.

13. The fucan-low endotoxin composition of any one of claims 1, 3, and 4, wherein the fucan-low endotoxin composition is a white solid.

14. The fucan-low endotoxin composition of any one of claims 1, 3 and 4, wherein the fucan-low endotoxin composition when dissolved in water at a concentration from 1 mg/mL through 100 mg/mL forms a solution that is clear and colorless.

15. An agent for treating a fibrous adhesion in an animal comprising the fucan-low endotoxin composition of any one of claims 1, 3 and 4.

16. A medically acceptable fucan-low endotoxin composition comprising a therapeutically effective amount of the fucan-low endotoxin composition according to any one of claims 1, 3 and 4 in a medically acceptable buffer or diluent.

17. A medically acceptable fucan-low endotoxin dosage comprising the medically acceptable fucan-low endotoxin composition of claim 16 wherein the medically acceptable fucan-low endotoxin dose has an endotoxin level below 250 EU.

18. The medically acceptable fucan-low endotoxin dosage of claim 17 wherein the medically acceptable fucan-low endotoxin dose has an endotoxin level below 50 EU.

19. The medically acceptable fucan-low endotoxin dosage of claim 17 wherein the medically acceptable fucan-low endotoxin dose has an endotoxin level below 20 EU.

20. The medically acceptable fucan-low endotoxin dosage of claim 17 wherein the medically acceptable fucan-low endotoxin dose has an endotoxin level below 2 EU.

21. The medically acceptable fucan-low endotoxin dosage of claim 17 wherein the medically acceptable fucan-low endotoxin dose has an endotoxin level below 0.1 EU.

22. The medically acceptable fucan-low endotoxin dosage of claim 17 wherein the medically acceptable fucan-low endotoxin dose has an endotoxin level below 0.01 EU.

23. The medically acceptable fucan-low endotoxin dosage of claim 17 wherein the fucan-low endotoxin composition comprises a fucan with a molecular weight distribution in which at least 60% w/w of the fucan has a molecular weight greater than 100 kDa, a weight average molecular weight of between 300 kDa and 5,000 kDa, a sulfation level between 20% w/w and 60% w/w, a carbohydrate content of between 30% w/w and 80% w/w, and a fucose content as a percentage of the total carbohydrate content of between 30% w/w to 100% w/w.

24. The medically acceptable fucan-low endotoxin dosage of claim 17 wherein the fucan-low endotoxin composition comprises a fucan with a molecular weight distribution in which at least 90% w/w of the fucan has a molecular weight greater than 100 kDa, a weight average molecular weight of between 600 kDa and 1,800 kDa, a sulfation level between 35% w/w and 60% w/w, a carbohydrate content of between 40% w/w and 65% w/w, and a fucose content as a percentage of the total carbohydrate content of at least about 80% w/w.

25. The medically acceptable fucan-low endotoxin dosage of claim 17 wherein the fucan-low endotoxin composition comprises a fucan with a molecular weight distribution in which at least 90% w/w of the fucan has a molecular weight greater than 100 kDa, a weight average molecular weight of between 600 kDa and 1,800 kDa, a sulfation level between 35% w/w and 52% w/w, a carbohydrate content of between 40% w/w and 65% w/w, and a fucose content as a percentage of the total carbohydrate content of at least about 80% w/w.

26. A medical composition comprising between about 0.02 mg/mL and 100 mg/mL of the fucan-low endotoxin composition of any one of claims 1, 3 and 4 wherein the medical composition is configured and composed to treat a disease or condition in an animal.

27. The medical composition of claim 26 wherein the disease or condition is a fibrous adhesion.

* * * * *